(12) United States Patent
You et al.

(10) Patent No.: US 8,772,031 B2
(45) Date of Patent: Jul. 8, 2014

(54) COMPOSITION FOR REPROGRAMMING SOMATIC CELLS TO GENERATE INDUCED PLURIPOTENT STEM CELLS, COMPRISING OCT4 IN COMBINATION WITH BMI1 OR ITS UPSTREAM REGULATOR, AND METHOD FOR GENERATING INDUCED PLURIPOTENT STEM CELLS USING THE SAME

(71) Applicant: Korea University Research and Business Foundation, Seoul (KR)

(72) Inventors: Seungkwon You, Yongin-Si (KR); Jai-Hee Moon, Seoul (KR); Jun Sung Kim, Guri-Si (KR); Byung Sun Yoon, Seoul (KR); Jung Han Lee, Anyang-Si (KR); Eun Kyoung Jun, Seongnam-Si (KR); June Seok Heo, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 0 days.

(21) Appl. No.: 13/890,896

(22) Filed: May 9, 2013

(65) Prior Publication Data
US 2013/0280808 A1 Oct. 24, 2013

Related U.S. Application Data

(62) Division of application No. 12/905,341, filed on Oct. 15, 2010, now abandoned.

(30) Foreign Application Priority Data

Dec. 30, 2009 (KR) .................. 10-2009-0134966
Dec. 30, 2009 (KR) .................. 10-2009-0134974
Dec. 30, 2009 (KR) .................. 10-2009-0134976
Dec. 30, 2009 (KR) .................. 10-2009-0134986

(51) Int. Cl.
| | | |
|---|---|---|
| *C12N 5/00* | (2006.01) | |
| *C12N 5/02* | (2006.01) | |
| *C12N 15/00* | (2006.01) | |
| *C12N 5/07* | (2010.01) | |
| *C12N 5/10* | (2006.01) | |
| *C12N 5/0735* | (2010.01) | |
| *C12N 5/071* | (2010.01) | |

(52) U.S. Cl.
CPC ........ *C12N 5/0606* (2013.01); *C12N 2501/602* (2013.01); *C12N 2501/60* (2013.01); *C12N 2501/41* (2013.01); *C12N 2501/603* (2013.01); *C12N 2510/00* (2013.01); *C12N 5/0696* (2013.01)
USPC ............ 435/377; 435/455; 435/354; 435/357

(58) Field of Classification Search
CPC ............... C12N 5/0696; C12N 5/0606; C12N 2501/41; C12N 2501/60; C12N 2501/603; C12N 2510/00; C12N 2501/602

USPC .................. 435/377, 455, 354, 357
See application file for complete search history.

(56) References Cited

U.S. PATENT DOCUMENTS

2008/0206286 A1 8/2008 Yu
2009/0047263 A1 2/2009 Yamanaka et al.

FOREIGN PATENT DOCUMENTS

KR 10-2007-0089018 8/2007
KR 10-2007-0089089 8/2007

OTHER PUBLICATIONS

Oliveri et al. Regenerative Medicine, 2(5): 795-816, Sep. 2007.*
Sullivan et al. Reproductive BioMed. Online, 16(1): 41-50, Nov. 2008.*
Takahashi et al., Cell, 126: 663-676, 2006.*
Kim et al., Nature, 461: 649-654, 2009.*
Wobus et al. (1997) J Mol. Cell Cardiology 29:1525.*
Xu et al. (2002) Circulation Research 91:50.*
Wobus et al. (1988) Biomed. Biochim Acta 12:965.*
Schuldiner (2000) PNAS 97:11307.*
Kramer et al. (2000) Mech. of Dev. 92:193.*
Johansson et al. (1995) Mol and Cell Biol. 15:141.*
Sato et al. (2004) Nat. Med. 10:55-63.*
Jacobs, et al. "Bmi-1 collaborates with c-Myc in tumorigenesis by inhibiting c-Myc-induced apoptosis via INK4a/ART," Genes & Development, (1999), vol. 13, pp. 2678-2690.
Banito, et al. "Senescence impairs successful reprogramming to pluripotent stem cells," Genes & Development, (2009), vol. 23, pp. 2134-2139.
Li, et al. "The INK4/Arf locus is a barrier for iPS cell reprogramming," Nature, (2009), vol. 460, pp. 1136-1141.
Kim, et al. "Direct reprogramming of human neural stem cells by OCT4," Nature, (2009), vol. 461, pp. 649-654.
Kawamura, et al. "Linking the p53 tumour suppressor pathway to somatic cell reprogramming," Nature, (2009), vol. 460, pp. 1140-1145.
Kim, et al., "OCT4-Induced pluripotency in Adult Neural Stem Cells," Cells, (2009), vol. 136, pp. 411-419.
European Search Report, Application No. EP 10 18 7898, mailed on May 20, 2011.
Moon et al., "Generation of Induced Pluripotent Stem Cells with Bmil and Oct4", 2009 Annual Meeting of Korean Society for Stem Cell Research (KSSCR)—Joint Symposium for Adult Stem Cell Research Center, SNU; Pluripotent Stem Cells, Nov. 5, 2009, Seoul, Korea, 3 pages.

* cited by examiner

*Primary Examiner* — Thaian N Ton
(74) *Attorney, Agent, or Firm* — Edwards Wildman Palmer LLP

(57) ABSTRACT

Disclosed is a composition for reprogramming somatic cells to generate embryonic stem cell-like cells, comprising: a) a Bmi1 (B cell-specific Moloney murine leukemia virus integration site 1) protein or a nucleic acid molecule coding for Bmi1; and b) an Oct4 protein or a nucleic acid molecule coding for Oct4. Also, a method is provided for reprogramming somatic cells to generate embryonic stem cell-like cells using the composition. In addition to reducing the number of the genetic factors conventionally needed, the composition and method allow the generation of pluripotent embryonic stem cell-like cells which have high potential in the cell therapy of various diseases.

1 Claim, 54 Drawing Sheets

FIG. 1
FIG. 1A
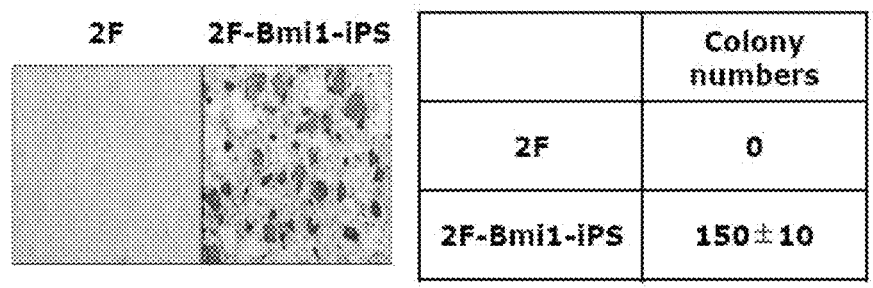
FIG. 1B
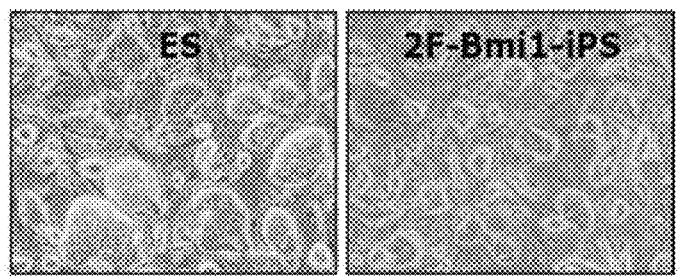

FIG. 1C
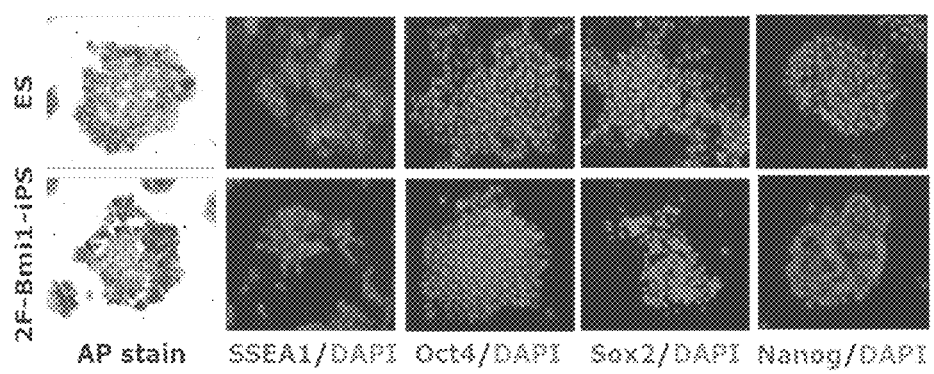
FIG. 2:
FIG. 2A
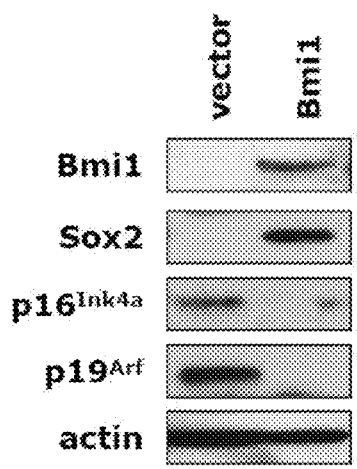

| | Colony numbers |
|---|---|
| Oct4 | 0 |
| Bmi1 and Oct4 (BO) | 50 ± 2 |

FIG. 6:
FIG. 6A
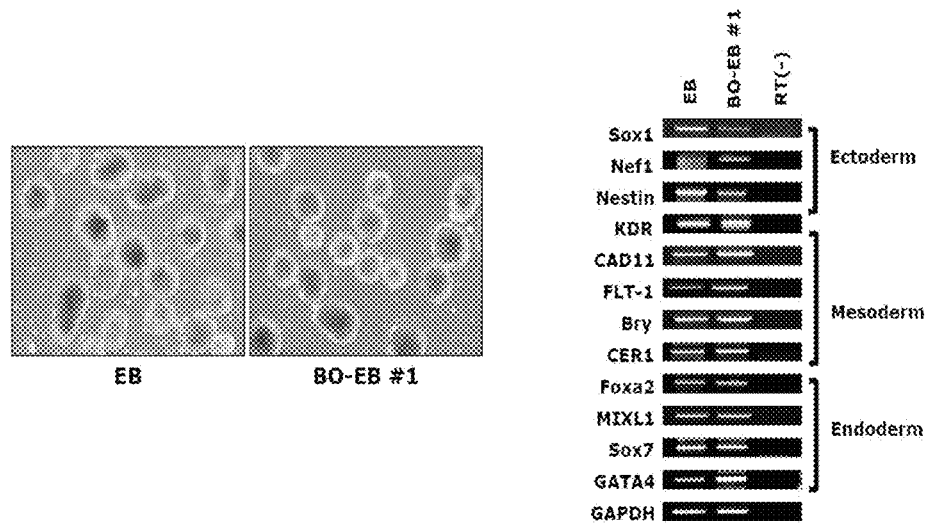
FIG. 6B
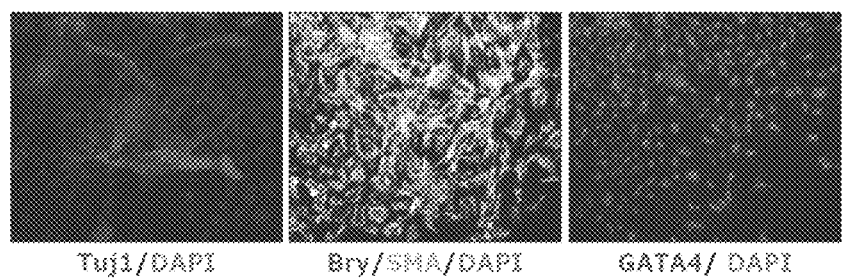

FIG. 7:
FIG. 7A
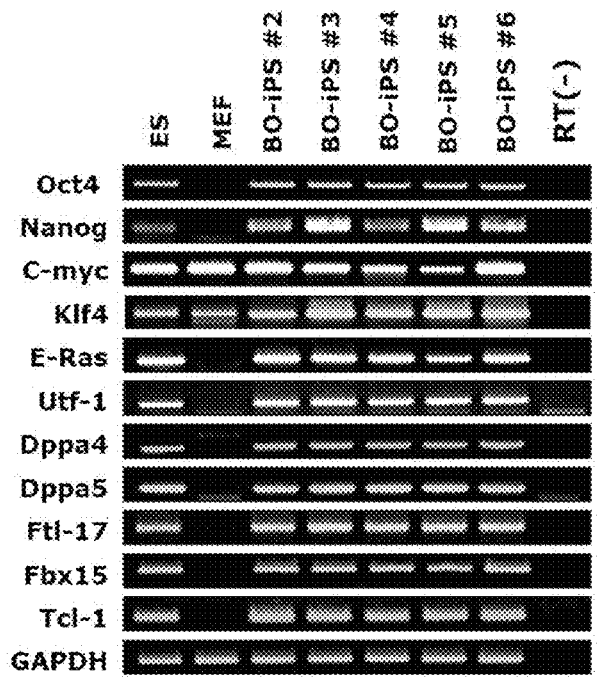
FIG. 7B
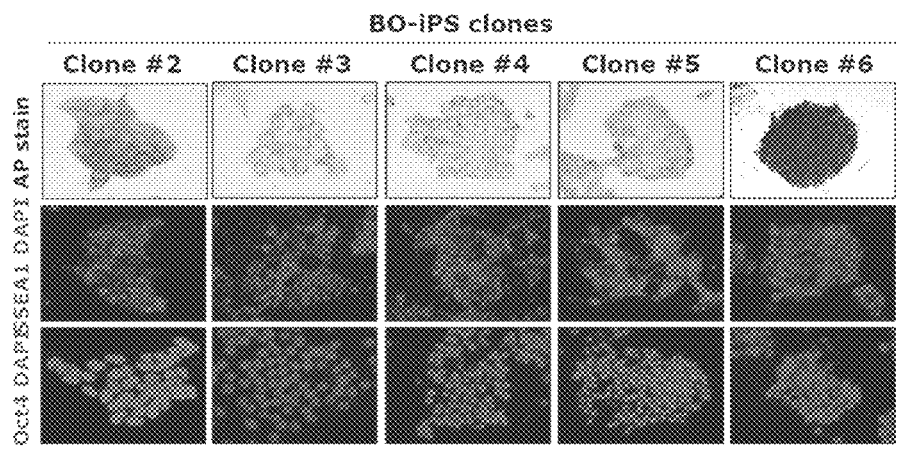

SEQUENCE LISTING

```
<160> NUMBER OF SEQ ID NOS: 2

<210> SEQ ID NO 1
<211> LENGTH: 3203
<212> TYPE: DNA
<213> ORGANISM: Homo sapiens

<400> SEQUENCE: 1
gagaggcaga gatcggggcg agacaatggg gatgtgggcg cgggagcccc gttccggctt      60
agcagcacct cccagccccg cagaataaaa ccgatcgcgc cccctccgcg cgcgccctcc     120
cccgagtgcg gagcgggagg aggcggcggc ggccgaggag gaggaggagg aggccccgga     180
ggaggaggcg ttggaggtcg aggcggaggc ggaggaggag gaggccgagg cgccggagga     240
ggccgaggcg ccggagcagg aggaggccgg ccggaggcgg catgagacga gcgtggcggc     300
cgcggctgct cggggccgcg ctggttgccc attgacagcg gcgtctgcag ctcgcttcaa     360
gatggccgct tggctcgcat tcattttctg ctgaacgact tttaactttc attgtctttt     420
ccgcccgctt cgatcgcctc gcgccggctg ctctttccgg gattttttat caagcagaaa     480
tgcatcgaac aacgagaatc aagatcactg agctaaatcc ccacctgatg tgtgtgcttt     540
gtggagggta cttcattgat gccacaacca taatagaatg tctacattcc ttctgtaaaa     600
cttgtattgt tcgttacctg gagaccagca agtattgtcc tatttgtgat gtccaagttc     660
acaagaccag accactactg aatataaggt cagataaaac tctccaagat attgtataca     720
aattagttcc agggcttttc aaaaatgaaa tgaagagaag aagggatttt tatgcagctc     780
atccttctgc tgatgctgcc aatggctcta atgaagatag aggagaggtt gcagatgaag     840
```

```
ataagagaat tataactgat gatgagataa taagcttatc cattgaattc tttgaccaga      900
acagattgga tcggaaagta aacaaagaca aagagaaatc taaggaggag gtgaatgata      960
aaagatactt acgatgccca gcagcaatga ctgtgatgca cttaagaaag tttctcagaa     1020
gtaaaatgga catacctaat actttccaga ttgatgtcat gtatgaggag gaacctttaa     1080
aggattatta tacactaatg gatattgcct acatttatac ctggagaagg aatggtccac     1140
ttccattgaa atacagagtt cgacctactt gtaaaagaat gaagatcagt caccagagag     1200
atggactgac aaatgctgga gaactggaaa gtgactctgg gagtgacaag gccaacagcc     1260
cagcaggagg agttccctcc acctcttctt gtttgcctag ccccagtact ccagtgcagt     1320
ctcctcatcc acagtttcct cacatttcca gtactatgaa tggaaccagc aacagcccca     1380
gcggtaacca ccaatcttct tttgccaata gacctcgaaa atcatcagta aatgggtcat     1440
cagcaacttc ttctggttga tacctgagac tgttaaggaa aaaaatttta aaccccctgat    1500 ttatatagat atcttcagcc attacgactt tctagagcta atacatgtga ctatcgtcca     1560
atttgctttc ttttgtagtg acattaaatt tggctataaa agatggacta catgtgatac     1620
tcctgtccgt cttggttcaa aagaaagatt gttgttataa agaattggtt tcttggaaag     1680
caggcaagac ttttttctctg tgttaggaaa gatgggaaat ggtttctgta accattgttt    1740
ggatttggaa gtactctgca gtggacataa gcattgggcc atagtttgtt aatctcaact     1800
aacgcctaca ttacattctc cttgatcgtt cttgttatta cgctgttttg tgaacctgta     1860
gaaaaacaag tgcttttat cttgaaattc aaccaacgga aagaatatgc atagaataat      1920
gcattctatg atgccatgtc actgtgaata acgatttctt gcagctattt agccattttg     1980
attgctgttt gatttatact tctctgttgc tacgcaaaac cgatcaaaga aaagtgaact     2040
tcagttttac aatctgtatg cctaaaagcg ggtactaccg tttattttac tgacttgttt     2100
aaatgattcg cttttgtaag aatcagatgg cattatgctt gttgtacaat gccatattgg     2160
tatatgacat aacaggaaac agtattgtat gatatatcta taaatgctat aaagaaatat     2220
tgtgtttcat gcattcagaa atgattgtta aaattctccc aactggttcg acctttgcag     2280
atacccataa cctatgttga gccttgctta ccagcaaaga atattttaa tgtggatatc      2340 taattctaaa gtctgttcca ttagaagcaa ttggcacatc tttctatact ttatatactt     2400
ttctccagta atacatgttt actttaaaaa ttgttgcagt gaagaaaaac ctttaactga     2460
gaaatatgga aaccgtctta attttccatt ggctatgatg gaattaatat tgtattttaa     2520
aaatgcatat tgatcactat aattctaaaa caatttttta aataaccag caggttgcta      2580 aaagaaggca ttttatctaa agttatttta ataggtggta tagcagtaat tttaaattta     2640
agagttgctt ttacagttaa caatggaata tgccttctct gctatgtctg aaaatagaag     2700
ctatttatta tgagcttcta caggtatttt taaatagagc aagcatgttg aatttaaaat     2760
atgaataacc ccacccaaca attttcagtt tatttttgc tttggtcgaa cttggtgtgt      2820
gttcatcagt tatttgtgag ggtgtttatt ctatatgaat attgtttcat gtttgtaggg    2880
aaattgtagc taaacatttc attgtcccca gtctgcaaaa gaagcacaat tctattgctt     2940
tgtcttgctt atagtcatta aatcattact tttacatata ttgctgttac ttctgctttc     3000
tttaaaaata tagtaaagga tgttttatga agtcacaaga tacatatatt tttattttga    3060
cctaaatttg tacagtccca ttgtaagtgt tgttttctaat tatagatgta aaatgaaatt    3120
tcatttgtaa ttggaaaaaa tccaataaaa aggatattca tttagaaaat agctaagatc     3180
```

```
tttaataaaa atttgatatg aaa                                              3203

<210> SEQ ID NO 2
<211> LENGTH: 1411
<212> TYPE: DNA
<213> ORGANISM: Homo sapiens

<400> SEQUENCE: 2
ccttcgcaag ccctcatttc accaggcccc cggcttgggg cgccttcctt ccccatggcg        60
ggacacctgg cttcggattt cgccttctcg cccctccag gtggtggagg tgatgggcca       120 gggggggccgg agccgggctg ggttgatcct cggacctggc taagcttcca aggccctcct     180
ggagggccag gaatcgggcc gggggttggg ccaggctctg aggtgtgggg gattccccca      240
tgccccccgc cgtatgagtt ctgtgggggg atggcgtact gtgggcccca ggttggagtg      300
gggctagtgc cccaaggcgg cttggagacc tctcagcctg agggcgaagc aggagtcggg      360
gtggagagca actccgatgg ggcctccccg gagccctgca ccgtcacccc tggtgccgtg      420
aagctggaga aggagaagct ggagcaaaac ccggaggagt cccaggacat caaagctctg      480
cagaaagaac tcgagcaatt tgccaagctc ctgaagcaga agaggatcac cctgggatat     540
acacaggccg atgtggggct caccctgggg gttctatttg ggaaggtatt cagccaaacg      600
accatctgcc gctttgaggc tctgcagctt agcttcaaga acatgtgtaa gctgcggccc      660
ttgctgcaga agtgggtgga ggaagctgac aacaatgaaa atcttcagga gatatgcaaa      720
gcagaaaccc tcgtgcaggc ccgaaagaga aagcgaacca gtatcgagaa ccgagtgaga      780
ggcaacctgg agaatttgtt cctgcagtgc ccgaaaccca cactgcagca gatcagccac      840
atcgcccagc agcttgggct cgagaaggat gtggtccgag tgtggttctg taaccggcgc      900
cagaagggca agcgatcaag cagcgactat gcacaacgag aggattttga ggctgctggg      960
tctcctttct caggggacc agtgtccttt cctctggccc cagggcccca ttttggtacc     1020
ccaggctatg ggagccctca cttcactgca ctgtactcct cggtcccttt ccctgagggg     1080
gaagcctttc ccctgtctc cgtcaccact ctgggctctc ccatgcattc aaactgaggt     1140
gcctgccctt ctaggaatgg gggacagggg gaggggagga gctagggaaa gaaaacctgg    1200
agtttgtgcc agggttttg ggattaagtt cttcattcac taaggaagga attgggaaca     1260
caaagggtgg gggcagggga gtttggggca actggttgga gggaaggtga agttcaatga     1320
tgctcttgat tttaatccca catcatgtat cacttttttc ttaaataaag aagcctggga    1380
cacagtagat agacacactt aaaaaaaaaa a                                    1411
```

COMPOSITION FOR REPROGRAMMING SOMATIC CELLS TO GENERATE INDUCED PLURIPOTENT STEM CELLS, COMPRISING OCT4 IN COMBINATION WITH BMI1 OR ITS UPSTREAM REGULATOR, AND METHOD FOR GENERATING INDUCED PLURIPOTENT STEM CELLS USING THE SAME

CROSS-REFERENCE TO RELATED APPLICATIONS

This application is a Divisional of U.S. Ser. No. 12/905,341, filed Oct. 15, 2010 and published as US 2011-0159592 A1 on Jun. 30, 2011. U.S. Ser. No. 12/905,341 claims priority to each of Korean Patent Application Ser. Nos. 10-2009-0134966, 10-2009-0134974, 10-2009-0134976, and 10-2009-0134986, each filed on Dec. 30, 2009. The entire contents of the aforementioned patent applications are incorporated herein by reference.

SEQUENCE LISTING

The instant application contains a Sequence Listing which has been submitted in ASCII format via EFS-Web and is hereby incorporated by reference in its entirety. Said ASCII copy, created on May 9, 2013, is named 90949-DIV-312617_Sequence_Listing_ST25.txt and is 6,905 bytes in size.

BACKGROUND OF THE INVENTION

1. Field of the Invention

The present invention relates to a composition for reprogramming somatic cells to generate induced pluripotent stem cells, comprising Oct4 in combination with Bmi1 or its upstream regulator and a method for generating induced pluripotent stem cells using the same. More particularly, the present invention relates to a technique in which when Oct4 is introduced, in combination with a reprogramming factor selected from among Shh (Sonic hedgehog), oxysterol and purmorphamine, they act in cooperation to induce the somatic cells to undergo a reprogramming process to generate induced pluripotent stem cells.

2. Description of the Related Art

Stem cells are characterized by self-renewal, that is, the ability to go through numerous cycles of cell division while maintaining a state of undifferentiation, and potency, that is, the capacity to differentiate into specialized cell types under suitable conditions. Potency specifies the differentiation potential of the stem cell, and is generally divided into pluripotency, multipotency and unipotency. Therefore, the technique of allowing the stem cells to undergo self-renewal in cell cultures and transforming them into specialized cells has high potential in the cell therapy of various diseases.

Present in adults, various stem cells including hematopoietic stem cells, bone marrow stem cells, and neural stem cells can be used in medical therapies without inducing immune rejection responses because they can be isolated from the patients themselves. In addition, cell therapy with adult stem cells solves the difficulty of securing donors for organ implantation.

Thus far, adult stem cells have been known to remain multipotent, that is, able to differentiate into a number of cells, but only those of a closely related family of cells. Many reports are to the effect that stem cells isolated from the central nervous system (Science 255, 1707-1710 1992; Science 287, 1433-1438 2000), the bone marrow (Science 276, 71-74, 1997; Science 287, 1442-1446, 2000; Science 284, 143-147, 1999), the retina (Science 287, 2032-2036, 2000) and the skeletal muscles (Proc. Natl. Acad. Sci. USA 96, 14482-14486, 1999; Nature 401, 390-394, 1999) are transformed into closely related tissue cells. For example, hematopoietic stem cells can be differentiated into blood-related cells, neural stem cells into neurons or glial cells, and bone marrow stem cells into mesodermal cells. Further, although theoretically they undergo infinite self-renewal adult stem cells are in practice difficult to proliferate in vitro. Moreover, practical limitations are imparted to the isolation of a number of cells from patients.

Pluripotent stem cells are a wonderful resource overcoming the drawbacks of adult stem cells. Pluripotent stem cells can differentiate into nearly any cell and are allowed to replicate infinitely in vitro. Among the pluripotent stem cells known thus far are embryonic stem cells, embryonic germ cells and embryonic carcinoma cells, with most studies focusing on embryonic stem cells for differentiation into specific cells, functionality in animal models of diseases, and therapeutic potency for various diseases.

Nonetheless, the clinical use of embryonic stem cells, like adult stem cells, encounters barriers that must be overcome. Above all, because isolating embryonic stem cells results in the death of the fertilized human embryo, this raises ethical issues. Also, there is the problem of immunological rejection when differentiated cells derived from embryonic stem cells are implanted into patients.

Various attempts have been made to overcome the above-mentioned problems. The greatest amount of attention has been paid to reprogramming differentiated cells into pre-differentiated cells, inter alia. Reprogramming is a generic term expressing the induction of differentiated cells to dedifferentiate into pluripotent stem cells such as embryonic stem cells, generally achieved by nuclear transfer, cell fusion, cell extract treatment, and induced pluripotent stem (iPS) cell technology (Cell 132, 567-582, 2008).

The iPS cell technology succeeded in generating cells closer to embryonic stem cells than has any other technology. Since 2006 in which iPS cells were first produced, a significant number of research articles have been issued. In principle, stem cells similar to embryonic stem cells, e.g., iPS cells, are derived by transfection of four genes (reprogramming inducing genes: Oct4, Sox2, Klf4, and C-Myc/Oct4, Sox2, Nanog, and Lin28) into mouse or human somatic cells, followed by culturing for a long period of time under conditions specialized for embryonic stem cells. These iPS cells have been shown to resemble embryonic stem (ES) cells in their gene expression profile, epigenetic status, in-vitro and in-vivo differentiation into all three germ layers, teratoma formation, chimeric mouse generation, and chimera's competency for germline transmission (Cell 126, 663-676, 2006; Science 318, 1917-1920, 2007).

However, the understanding of the molecular mechanisms underlying reprogramming is meager, which is largely attributed to the use of too many gene factors. To realize the full potential of iPS cells in practical clinical use, it will be essential to improve the reprogramming technology, although established, and to evaluate each generated iPS cell line for safety and efficacy.

Recent research reports have it that the inactivation of the tumor suppressor gene p53 markedly increases the efficiency of iPS cell generation (Nature 460, 1132-1135, 2009). p19$^{Arf}$ and p16$^{Ink4a}$, both encoded by alternative reading frames of Arf/Ink4a locus, are known to induce the expression of p53 and Rb, respectively. By reducing the expression of both $p16^{Ink4a}$ and $p19^{Arf}$, iPS cell formation was increased relative to that attained by reducing the expression of $p19^{Arf}$ alone (Nature, 460, 1140-1144, 2009).

Polycomb group (PcG) proteins are epigenetic gene silencers. Bmi1, one of the PcG proteins, is involved in the down-regulation of both $p16^{Ink4a}$ and $p19^{Arf}$, which leads to suppressing the expression of p53 and Rb (Genes Dev, 2678-2690, 1999). Further, Bmi1 is known to regulate the expression of target genes by modifying chromatin organization. These functions allow Bmi1 to play an important role in the self-renewal of neural stem cells and hematopoietic stem cells. Based on this, the present inventors succeeded in the reprogramming of astrocytes to induce neural stem cells by overexpressing Bmi1 therein. The induced neural stem cells were similar in many aspects to those isolated from mice. Inter alia, the induced neural stem cells were found to have an increased expression level of Sox2, a gene essential for the self renewal of neural stem cells (Biochem Biophys Res Commun. 371, 267-272, 2008).

Somatic cells require four (Oct4, Sox2, Klf4, C-Myc) or three (Oct4, Sox2, Klf4) genes for their dedifferentiation. It is known that these genes may not be additionally introduced into the cells which endogenously express them. Representatively, it was demonstrated that the introduction of Oct4 alone induces the generation of iPS cells from mouse/human neural cells since they show the endogenous expression of Sox2, Klf4 and C-Myc (Nature, 461, 649-653, 2009). Nowhere has, however, the process of generating pluripotent embryonic stem cell-like cells with Oct4 factor alone been known in the art.

SUMMARY OF THE INVENTION

The present inventors hypothesized that induced pluripotent stem cells could be established by Oct overexpression in combination with Bmi1 overexpression which results in the induction of Sox2 and the down-regulation of $p16^{Ink4a}$ and $p19^{Arf}$. On the basis of this hypothesis, the two genes were introduced into somatic cells which were then cultured in a condition used to culture embryonic stem cells. As a consequence, cell lines resembling embryonic stem cells were established. It was found that there was a high similarity in various properties including gene expression, epigenetics, in-vitro/in-vivo differentiation into all three germ layers, teratoma formation, and chimeric mouse generation between the established cell lines and embryonic stem cells.

Further, the present inventor thought that the employment of an upstream regulator of Bmi1 might reduce the number of the genes conventionally needed for reprogramming. Shh (Sonic hedgehog), an upstream regulator of Bmi1, and its analogs were observed to provide the same results as in the Bmi1 gene overexpression system.

It is therefore an object of the present invention to provide a composition for reprogramming somatic cells to generate embryonic stem cell-like cells, comprising Oct4 gene in combination with Bmi1 or its upstream regulator such as Shh or its analogs.

It is another object of the present invention to provide a method for reprogramming somatic cells to generate embryonic stem cell-like cells by introducing an Oct4 gene in combination with Bmi1, Shh or a Shh analog.

It is a further object of the present invention to provide embryonic stem cell-like cells generated by the method.

BRIEF DESCRIPTION OF THE DRAWINGS

The above and other objects, features and other advantages of the present invention will be more clearly understood from the following detailed description taken in conjunction with the accompanying drawings, in which:

FIG. 1 shows reprogramming efficiencies upon the introduction of the two factors Oct4 and Sox2 genes (2F), and the three factors Oct4, Sox2 and Bmi1 genes (2F-Bmi1) into mouse embryonic fibroblasts.

FIG. 1A shows generation frequencies of iPS cells upon the introduction of two factors (Oct4 and Sox2) and three factors (Bmi1, Oct4 and Sox2) as measured by AP (alkaline phosphatase) staining. AP-positive colonies were generated from cells infected with 2F-Bmi1 (2F-Bmi1-Ips), but not 2F (left) and numbered (right).

FIG. 1B shows the morphology of established 2F-Bmi1-iPS cells, which is similar to that of ES cells.

FIG. 1C shows the expression of SSEA1, Oct4, Sox2 and Nanog, specific for embryonic stem cells, in mES cells (upper panels) and 2F-Bmi1-iPS cells (lower panels), as detected by immunochemical staining. AP-positive colonies are also detected in both.

FIG. 2 shows the dedifferentiation of mouse embryonic fibroblasts into neural stem cells by retroviral transduction with Bmi1.

FIG. 2A shows the expression of Bmi1 in the mouse embryonic fibroblasts, with an increase in the expression level of Sox2 and a decrease in the expression level of the Bmi1 target genes $p16^{Ink4a}$ and $p19^{Arf}$.

FIG. 6 shows in-vitro and in-vivo differentiation into all three germ layers.

FIG. 6A shows the embryonic body (EB) formation of the induced stem cells, and the expression of markers characteristic of the three germ layers as measured by RT-PCR.

FIG. 6B shows the spontaneous differentiation of the embryonic bodies into respective cells representative of the three germ layers, as analyzed by immunocytochemistry for markers typical of the three germ layers. The embryonic bodies differentiated into endoderm, mesoderm and ectoderm cells which are characterized by the expression of GATA4, Bry, SMA, and Tuj1.

FIG. 7 shows comparison between ES cells and clones obtained from a homogenous population of iPS cells.

FIG. 7A shows the expression profiles of main genes essential for embryonic stem cells in MEF and iPS cells as measured by RT-PCR.

FIG. 7B shows the detection of positive AP staining and markers at the clones, as measured by immunocytochemistry.

DESCRIPTION OF THE PREFERRED EMBODIMENTS

Figure 2B:
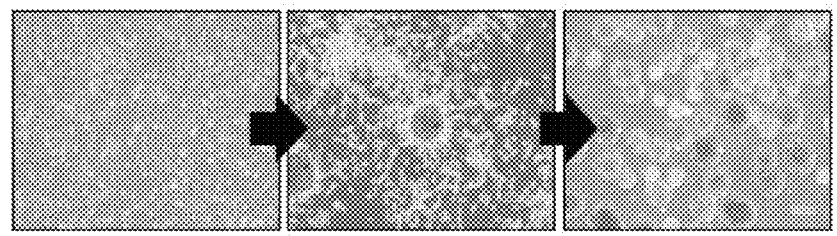
FIG. 2B shows that when cultured in the conditions used for neural stem cells, Bmi1-induced mouse embryonic fibroblasts started to aggregate on day 3 and changed their morphology to those of neurospheres on day 7.
Figure 2C:
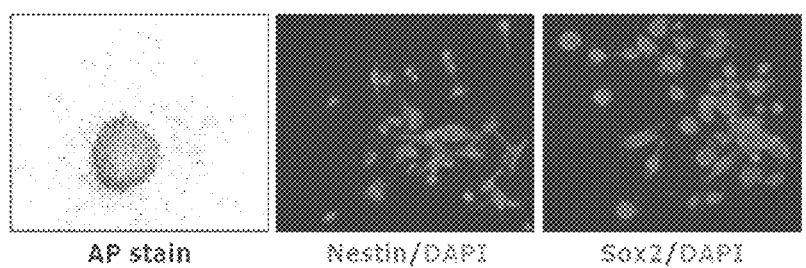
FIG. 2C shows the characterization of neural stem cell-like cells by AP-staining and immunocytochemistry for Nestin and Sox2, markers specific for neural stem cells.
Figure 2D:
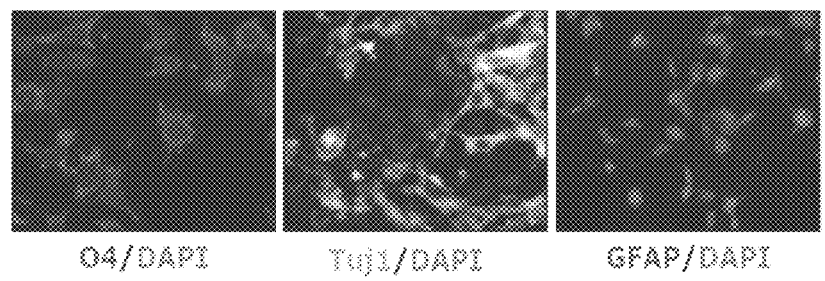
FIG. 2D shows the multipotency of the neural stem cell-like cells derived from Bmi1-induced mouse embryonic stem cells to differentiate into neurons, oligodendrocytes and astrocytes as measured by immunocytochemistry for their respective representative markers Tuj1, O4, and GFAP.

Leading to the present invention, intensive and thorough research into dedifferentiation of somatic cells, conducted by the present inventors, aiming to overcome the problems encountered in the prior arts, resulted in the finding that when introduced into the somatic cells, Oct4 in combination with a reprogramming factor selected from among Shh or a Shh analog such as oxysterol or purmorphamine, can induce the somatic cells to undergo dedifferentiation into pluripotent embryonic stem cell-like cells.

In accordance with an aspect thereof, the present invention provides a composition for reprogramming somatic cells to generate embryonic stem cell-like cells, comprising:

a) a Bmi1 (B cell-specific Moloney murine leukemia virus integration site 1) protein or a nucleic acid molecule coding for Bmi1; and b) an Oct4 protein or a nucleic acid molecule coding for Oct4.

As used herein, the term "embryonic stem cell (ESC)-like cell" is intended to refer to a pluripotent cell characterized by the properties of ESC including, but not being limited to, proliferation without transformation, infinite replication, self-renewal and differentiation into all three germ layers. In this context, the embryonic stem cell-like cells are used interchangeably with embryonic stem cells or induced pluripotent stem cells.

When inducing the generation of embryonic stem cell-like cells, no special limitations are imparted to starting somatic cells. As long as the somatic cell is induced to undergo dedifferentiation, any somatic cell may be employed. For example, somatic cells in the embryonic period or matured somatic cells may be employed. When the embryonic stem cell-like cells are applied to the treatment of diseases, it is desirable that they be derived from somatic cells of the patients, e.g., somatic cells related to diseases or involved in disease treatment. Preferably, the somatic cells are fibroblasts which may be isolated from animals, preferably mammals, including humans, mice, horses, sheep, pigs, goats, camels, antelopes, dogs, etc.

In accordance with an embodiment of the present invention, Bmi1 and Oct4 may be in the form of a protein or a nucleic acid molecule. Examples of the Bmi1 and the Oct4 useful in the present invention include those from animals including humans, mice, horses, sheep, pigs, goats, camels, antelopes, dogs, etc. with there being a preference for human Bmi1 and Oct4. In addition, Bmi1 and Oct4 proteins useful for dedifferentiation into embryonic stem cell-like cells may have their own wild-type amino acid sequences or variants.

Bmi1 and Oct4 protein variants refer to proteins which are different in amino acid sequence from wild-type proteins as a result of deletion, insertion, non-conservative or conservative substitution or a combination thereof at one or more amino acid residues while remaining biologically and functionally equivalent thereto with or without modification in physiochemical properties. If modified, the variants may have increased structural stability in the face of physical and chemical conditions as well as increased physiological activity.

In a preferred embodiment of the present invention, Bmi1 and Oct4 are provided as nucleotide sequences encoding the proteins.

The nucleotide sequences may encode wild-type or variant proteins of Bmi1 and Oct4 and may be modified at one or more nucleotide residues by substitution, deletion, insertion or a combination thereof. They may be isolated from nature or chemically synthesized.

The nucleotide sequences encoding Bmi1 and Oct4 may be DNA molecules (genomic DNA, cDNA) or RNA molecules in the form of single- or double-strands.

In accordance with a preferred embodiment of the present invention, the composition for reprogramming somatic cells into embryonic stem cell-like cells further comprises a vector carrying and expressing Bmi1 and Oct4 genes.

As used herein, the term "vector" refers to a DNA construct in which a gene of interest is operably linked to a regulatory element so that the gene can be expressed in a proper host which anchors the vector therein.

The term "operably linked", as used herein, is intended to refer to a functional linkage between a regulatory element and a nucleotide sequence encoding a protein of interest in such a functional relationship that the element can serve to initiate and mediate the transcription of the nucleotide sequence. In a recombinant vector, the functional linkage may be obtained using a genetic recombination technique well known in the art. Site-specific DNA cleavage and linkage may be accomplished with typical enzymes.

The regulatory element of the vector useful in the present invention may include a signal or leader sequence for membrane targeting or secreting as well as expression regulatory elements such as a promoter, an operator, an initiation codon, a stop codon, a polyadenylation signal and an enhancer, depending on the purpose thereof. The promoter may be constitutive or inducible. Further, the expression vector may contain a selection marker for selecting host cells transformed therewith. If replicable, the expression vector will contain a replication origin. The vector may be self-replicable or may be integrated into the chromosome of the host cell.

Among the vectors useful in the present invention are plasmids, cosmids, and viral vectors, there being a preference for viral vectors. Examples of the viral vectors include, but are not limited to, those derived from retrovirus, such as HIV (Human immunodeficiency virus), MLV (Murineleukemia virus), ASLV (Avian sarcoma/leukosis), SNV (Spleen necrosis virus), RSV (Rous sarcoma virus) and MMTV (Mouse mammary tumor virus), adenovirus, adeno-associated virus, and herpes simplex virus. In an embodiment of the present invention, a Bmi1 gene is inserted into a pBbe puro vector, that is, an MLV (Moloney leukemia virus)-based viral vector with a selection marker for puromycin while a pBabe neo vector, which is an MLV-based viral vector containing a selection marker for neomycin, is employed to carry and express an Oct4 gene.

In the present invention, the nucleotide sequences encoding Bmi1 and Oct4 may be introduced into host cells using a technique well known in the art, such as in the form of naked DNA vector (Wolff et al., Science, 1990: Wolffet al. J Cell Sci. 103:1249-59, 1992) or with the aid of liposomes or cationic polymers. A liposome is a phospholipid membrane for gene transfer, comprised of a mixture of cationic phospholipids such as DOTMA and DOTAP. A nucleic acid-liposome complex which is suitable for gene transfer across the cell membrane is formed when cationic liposomes are mixed with anionic nucleic acid molecules in a certain ratio.

In accordance with another preferred embodiment of the present invention, the composition for reprogramming somatic cells to generate embryonic stem cell-like cells further comprises a virus anchoring and expressing nucleotide sequences coding for Bmi1 and Oct4.

In this context, the term "virus" is that prepared by transfecting and infecting a packaging cell with a viral vector carrying genes encoding Bmi1 and Oct4.

Examples of the virus useful for the preparation of a virus expressing Bmi1 and Oct4 include, but are not limited to, retrovirus, adenovirus, adeno-associated virus, and herpes simplex virus, with a preference for retrovirus. In an embodiment of the present invention, a pBabe puro Bmi1 vector constructed by inserting a Bmi1-encoding nucleotide sequence (SEQ ID NO.: 1) into a pBabe puro vector and a pBabe neo Oct4 vector constructed by inserting an Oct4-encoding nucleotide sequence (SEQ ID NO.: 2) are transfected into PT67 packaging cell line to produce viruses expressing Bmi1 and Oct4 which are then used to infect fibroblasts. Virus packaged from PT67 cells shows high viral titers and can be used to infect a broad range of mammalian cells.

In accordance with another aspect thereof, the present invention provides a method for generating embryonic stem cell-like cells from somatic cells, comprising introducing both a Bmi1 (B cell-specific Moloney murine leukemia virus integration site 1) gene and an Oct4 gene into the somatic cells.

In greater detail, the method comprises (i) culturing fibroblasts in a medium; (ii) infecting the fibroblasts with a packaging cell into which respective vectors carrying a Bmi1 gene and an Oct4 gene are transfected; and (iii) culturing the infected fibroblasts under the conditions used to culture embryonic stem cells.

The medium used in step (i) is the medium usually used for culturing fibroblasts. Typically, the medium contains a carbon source, a nitrogen source, and trace elements. In a preferred embodiment of the present invention, fibroblasts are cultured in DMEM (high glucose, w/o sodium pyruvate) supplemented with 10% FBS (Fetal bovine serum), 0.1 mM nonessential amino acid, 1% penicillin/streptomycin and 0.1 mM β-mercaptoethanol.

In step (ii), a pBabe puro Bmi1 vector constructed by inserting a Bmi1-encoding nucleotide sequence into a pBabe puro vector and a pBabe neo Oct4 vector constructed by inserting an Oct4-encoding nucleotide sequence into a pBabe neo vector are transfected into packaging cells which allow the production of high-titer viruses capable of infecting a broad spectrum of mammalian host cells, to produce viruses which are then used for infection into fibroblasts. Bmi1 and Oct4 or nucleotides sequences encoding them may be of wild-type or variants thereof derived from animals including humans, mice, horses, sheep, pigs, goats, camels, antelopes, dogs, etc. In a preferred embodiment, human Bmi1 (NCBI accession No. L13689; SEQ ID NO.: 1) and human Oct4 (NCBI accession No. NM_002701; SEQ ID NO.: 2) are employed.

So long as it is typically used to culture embryonic stem cells, any medium may be employed in step (iii). In a preferred embodiment, the infected fibroblasts are cultured in high-glucose DMEM supplemented 15% FBS (Fetal bovine serum)+0.1 mM nonessential amino acid+1% penicillin/streptomycin+0.1 mM (3-mercaptoethanol+1000 unit/ml mouse LIF (leukemia inhibitory factor) in the presence of feeder cells, with a passage every two or three days.

In accordance with a further aspect thereof, the present invention provides an embryonic stem cell-like cell prepared by the method of the present invention.

The embryonic stem cell-like cell prepared by the method of the present invention is found to have a positive response to antibodies against the embryonic stem cell markers alkaline phosphatase, SSEA-1, Oct-4, and Sox2 and to express genes essential for maintaining the self-renewal of embryonic stem cells (Oct4, Sox2, Nanog, c-myc, Klf4) in a pattern similar to that of embryonic stem cells. Further, the embryonic stem cell-like cell according to the present invention exhibits the same pluripotency as typical embryonic stem cells. Moreover, the embryonic stem cell-like cell according to the present invention is characterized by self-renewal.

Accordingly, the embryonic stem cell-like cells of the present invention may serve as a source for various types of cells. For example, when cultured under conditions used for cell differentiation, the embryonic stem cell-like cells may be induced to differentiate into hematopoietic cells, neurons, beta cells, hepatocytes, chondrocytes, epithelial cells, urothelial cells, and analog cells thereof.

With regard to conditions, media and methods for differentiation of the embryonic stem cells, reference may be made to Palacios, et al., PNAS. USA, 92:7530-7537 (1995), Pedersen, J. Reprod. Fertil. Dev., 6; 543-552 (1994), and Bain et al., Dev. Biol, 168:342-357 (1995). Through implantation, the embryonic stem cells may be applied to the treatment of a number of diseases including diabetes mellitus, Parkinson's disease, Alzheimer's disease, cancer, spinal cord injury, multiple sclerosis, amyotrophic lateral sclerosis (Lou Gehrig's disease), muscular dystrophy, hepatic diseases, hypercholesterolemia, cardiac diseases, cartilage diseases, wounds, foot ulcer, gastroenteric disorders, vascular diseases, renal diseases, uterine diseases, senescence-related diseases, etc. Besides, the embryonic stem cell-like cells of the present invention may be useful for the evaluation of drugs.

In accordance with still a further aspect thereof, the present invention provides a method for generating induced neural stem cells from somatic cells, comprising introducing a Bmi1 (B cell-specific Moloney murine leukemia virus integration site 1) gene into the somatic cells and culturing the somatic cells under conditions used for neural stem cells.

The dedifferentiation of the somatic cells into neural stem cells was identified by the detection of specific markers (Nestin and Sox2). When subjected to typical differentiation conditions, the induced neural stem cells were found to differentiate into astrocytes, neurons, and ologidendrocytes as measured by immunochemical staining for respective markers GFAP, Tuj1 and O4.

In accordance with still a further aspect thereof, the present invention provides a composition for reprogramming somatic cells to generate embryonic stem cells, comprising:

a) an upstream regulator of Bmi1 selected from the group consisting of a Shh (Sonic hedgehog signaling) protein, a Shh-encoding nucleic acid molecule, oxysterol, purmorphamine and a combination thereof; and b) Oct4 protein or an Oct4-encoding nucleic acid molecule.

Bmi1 is regulated by the upstream regulator Shh (Sonic hedgehog) signaling pathway. If an experiment with Shh or a Shh analog provide a result similar to that obtained by an overexpression system of Bmi1, there might be a likelihood of reducing the number of the genes to be used for reprogramming. No reports have disclosed the generation of induced PS cells from fibroblasts with single genes alone, so far. Therefore, this approach may lead to a novel method for inducing dedifferentiation and further to a technique on the basis of which a method can be provided for generating iPS cells without introducing genes.

This hypothesis allowed the Shh signaling pathway to be used to overexpress Bmi1. Shh, a cytokine playing an important role in the self-renewal of neural stem cells, is reported to directly influence Gli1 transcription and to upregulate the expression of Bmi1 and Sox2, main factors of neural stem cells (Curr Mol Med. 9, 873-886, 2009; Crit Rev Oncol Hematol. 65, 43-53, 2008). Using knowledge contained in these reports, the present inventors disclosed in an academic article that the introduction of Bmi1 induces astrocytes to be reprogrammed into neural stem cells, the content of which was patented. Also, Shh was found to induce dedifferentiation. The content of the papers were was patented. When transferred into the culture conditions used for neural stem cells, murine fibroblasts that had been transfected with a Bmi1 gene were reprogrammed into neural stem cells, and this process was monitored by the expression of nestin and Sox2, markers characteristic of neural stem cells. In addition, the induced neural stem cells were found to differentiate into astrocytes, oligodendrocytes and neurons as measured by immunological staining for markers respectively specific therefor. It was also true of Shh treatment that Bmi1 expression was induced, initiating the generation of induced neural stem cells from somatic cells.

Based on this, the introduction of Oct4 while treating with Shh followed by culturing under the conditions of embryonic stem cells established embryonic stem cell-like cells which were found to highly resemble mouse embryonic stem cells in gene expression profile, epigenetic status, in-vitro and in-vivo differentiation into all three germ layers, and teratoma formation.

In accordance with an embodiment of the present invention, Shh and Oct4 may be in the form of a protein or a nucleic acid molecule. Examples of the Shh and the Oct4 useful in the present invention include those from animals including humans, horses, sheep, pigs, goats, camels, antelopes, dogs, etc. with a preference for human Shh and Oct4. In addition, Shh and Oct4 proteins useful for dedifferentiation into embryonic stem cell-like cells may have their own wild-type amino acid sequences or variants thereof.

Shh and Oct4 protein variants refer to proteins that have a different amino acid sequence than wild-type proteins as a result of deletion, insertion, non-conservative or conservative substitution or a combination thereof at one or more amino acid residues while remaining biologically functionally equivalent thereto with or without modification in physiochemical properties. If modified, the variants may have an increased structural stability in the face of physical and chemical conditions as well as increased physiological activity.

Preferably, Shh is provided as a protein. For example, the reprogramming of somatic cells into embryonic stem cell-like cells may be conducted by treating a medium therefor with a Shh protein. In addition to inducing Bmi1 expression, Shh, if provided as a protein, can reduce the number of the genes to be introduced for reprogramming.

An effective amount of Shh protein should be contained in a medium. The effective amount of Shh protein may vary depending on well-known factors including the kind of culture media, culture methods, etc. In a preferred embodiment of the present invention, Shh is used in an amount of 500 ng/ml.

In an embodiment of the present invention, Shh and Oct4 are provided as nucleotide sequences encoding the proteins.

The nucleotide sequences may encode wild-type or variant proteins of Shh and Oct4 and may have had one or more nucleotide residues modified as a result of substitution, deletion, insertion or a combination thereof. They may be isolated from nature or chemically synthesized.

The nucleotide sequences encoding Shh and Oct4 may be DNA molecules (genomic DNA, cDNA) or RNA molecules in the form of single- or double-strands.

In accordance with a preferred embodiment of the present invention, the composition for reprogramming somatic cells into embryonic stem cell-like cells further comprises a vector carrying and expressing Shh and Oct4 genes.

In accordance with another preferred embodiment of the present invention, the composition for reprogramming somatic cells to generate embryonic stem cell-like cells further comprises Shh protein and a virus anchoring and expressing nucleotide sequences coding for Oct4.

Alternatively, a Shh analog, such as hydroxycholesterol (oxysterol) or purmorphamine, may be employed, instead of Shh, to induce Shh signals (Stem cells 27, 703-713, 2009). Under a culture condition for neural stem cells, the treatment of mouse embryonic fibroblast with oxysterol or purmorphamine was observed to induce an increase in Bmi1 expression level and in turn in Sox2 expression level. Simultaneously, $p16^{Ink4a}$ and $p19^{Arf}$, both of which are targets of Bmi1, were down-regulated. Hence, treatment with oxysterol or purmorphamine induces the up-regulation of Bmi1 and Sox2 and the down-regulation of the target genes of Bmi1. The cells induced by treatment with oxysterol or purmorphamine were observed to have morphology similar to that of neural stem cells and express nestin and sox2, markers characteristic of neural stem cells. These results are the same as those that happen in the case of Bmi1 overexpression, indicating that the Shh analog oxysterol or purmorphamine can be used to induce somatic cells to undergo dedifferentiation into embryonic stem cell-like cells. This approach also has the advantage of reducing the number of genes that are introduced for reprogramming. The introduction of Oct4 while treating with the Shh analog followed by culturing under the conditions used for embryonic stem cells established embryonic stem cell-like cells which were found to highly resemble mouse embryonic stem cells in morphology, gene expression profile, epigenetic status, in-vitro and in-vivo differentiation into all three germ layers, teratoma formation and chimeric mouse generation.

Oxysterol, a Shh analog useful in the present invention, is also known as hydroxycholesterol, an oxidized derivative of cholesterol. Oxysterol is reported to play an important role in the pathophysiology of biliary diseases including acute and chronic inflammation, cholelithiasis, cholangiocarcinoma, etc. A recent report has it that the formation of dopamine-producing neurons during brain development is dependent on the activation of a specific receptor in the brain by oxysterol. Nowhere has the use of oxysterol in the generation of embryonic stem cell-like cells through dedifferentiation been reported in previous documents thus far.

No special limitations are imposed on the oxysterol for use in the present invention. So long as it functions to induce a Shh signal, any hydroxycholestrol may be used as a Shh analog useful in the present invention. For example, commercially available 25-, 7β-, and 19-hydroxycholesterol may be employed as Shh analogs.

The reprogramming of somatic cells into neural stem cell-like cells may be conducted by treating a medium therefor with oxysterol. In addition to inducing Bmi1 expression, oxysterol can reduce the number of genes that are introduced for reprogramming.

An effective amount of oxysterol should be contained in a medium. The effective amount of oxysterol may vary depending on well-known factors including the kind of culture media, culture methods, etc. In a preferred embodiment of the present invention, oxysterol is used in an amount of from 0.1 μM to 0.5 μM.

Purmorphamine, a purine compound, is involved in the Shh signaling pathway.

So long as it induces a Shh signal, any purmorphamine derivative may be used in the present invention, without particular limitations. For example, commercially available 2-(1-Naphthoxy)-6-(4-morpholinoanilino)-9-cyclohexylpurine may be used.

The reprogramming of somatic cells into neural stem cell-like cells may be conducted by treating a medium therefor with purmorphamine. In addition to inducing Bmi1 expression, oxysterol can reduce the number of the genes that are introduced for reprogramming.

An effective amount of purmorphamine should be contained in a medium. The effective amount of purmorphamine may vary depending on well-known factors including the kind of culture media, culture methods, etc. In a preferred embodiment of the present invention, oxysterol is used in an amount of from 0.5 μM to 1 μM.

In accordance with yet a further aspect thereof, the present invention provides a method for reprogramming somatic cells to generate embryonic stem cell-like cells, comprising treating the somatic cells with an upstream regulator of Bmi1 selected from the group consisting of Shh (Sonic hedgehog), a Shh-encoding nucleotide sequence, oxysterol, purmorphamine and a combination thereof, and introducing an Oct4 gene into the somatic cells.

In greater detail, the method comprises (i) culturing fibroblasts in a medium; (ii) treating the somatic cells with an upstream regulator of Bmi1 selected from the group consisting of Shh (Sonic hedgehog), a Shh-encoding nucleotide sequence, oxysterol, purmorphamine and a combination thereof while infecting the somatic cells with a packaging cell transfected with a vector carrying an Oct4 gene; and (iii) culturing the infected fibroblasts under the conditions used to culture embryonic stem cells.

The medium used in step (i) is a medium usually used for culturing fibroblasts. Typically, the medium contains a carbon source, a nitrogen source, and trace elements. In a preferred embodiment of the present invention, fibroblasts are cultured in DMEM (high glucose, w/o sodium pyruvate) supplemented with 10% FBS (Fetal bovine serum), 0.1 mM non-essential amino acid, 1% penicillin/streptomycin and 0.1 mM 8-mercaptoethanol.

In step (ii), an Oct4 gene is preferably introduced into fibroblasts while they are reprogrammed into neural stem cells by treatment with Shh, oxysterol or purmorphamine under the culturing conditions of neural stem cells. In this regard, fibroblasts are treated for one day with oxysterol or purmorphamine, after which they are infected three times at regular intervals of 16 hrs with an Oct4 virus while continuing to be treated with Shh, oxysterol or purmorphamine. While being treated with Shh, oxysterol or purmorphamine for a total time period of 72 hrs, the culture condition is changed from one suitable for neural stem cells to one suitable for embryonic stem cells so as to increase the reprogramming efficiency.

In step (ii), a pBabe neo Oct4 constructed by inserting an Oct4-encoding nucleotide sequence into a pBabe neo vector are transfected into PT67 packaging cells which allow the production of high-titer viruses capable of infecting a broad spectrum of mammalian host cells, to produce viruses which are then used to infect fibroblasts. Shh and Oct4 or nucleotides sequences encoding them may be of the wild-type or variants thereof derived from animals including humans, horses, sheep, pigs, goats, camels, antelopes, dogs, etc. In a preferred embodiment, human Oct4 (NCBI accession No. NM_002701; SEQ ID NO.: 2) is employed.

So long as it is typically accepted for culturing embryonic stem cells, any medium may be employed in step (iii). In a preferred embodiment, the infected fibroblasts are cultured in high-glucose DMEM supplemented 15% FBS (Fetal bovine serum)+0.1 mM nonessential amino acid+1% penicillin/streptomycin+0.1 mM β-mercaptoethanol+1000 unit/ml mouse LIF (leukemia inhibitory factor) in the presence of feeder cells, with a passage every two or three days.

In accordance with yet still another aspect thereof, the present invention provides an embryonic stem cell-like cell prepared by this method.

The embryonic stem cell-like cell prepared by the method of the present invention is found to positively respond to antibodies against the embryonic stem cell markers alkaline phosphatase, SSEA-1, Oct-4, and Sox2 and to express genes essential for maintaining the self-renewal of embryonic stem cells (Oct4, Sox2, Nanog, c-myc, Klf4) in a pattern similar to that of embryonic stem cells. Further, the embryonic stem cell-like cell according to the present invention exhibits the same pluripotency as typical embryonic stem cells.

A better understanding of the present invention may be obtained through the following examples which are set forth to illustrate, but are not to be construed as limiting the present invention.

Example 1

Culture of Mouse Embryonic Fibroblasts and Introduction of Oct4 and Bmi1 Genes Therein Mouse embryonic fibroblasts were employed to generate embryonic stem cell-like cells. Embryos were taken from CF1 strain mice on embryonic day 13.5. Cells were cultured in DMEM (high glucose, w/o sodium pyruvate) supplemented with 10% FBS (Fetal bovine serum), 0.1 mM nonessential amino acid, 1% penicillin/streptomycin and 0.1 mM β-mercaptoethanol in tissue culture flasks, after which fibroblasts at the $3^{rd}$ passage were seeded at a density of $2\times10^5$ cells/well into 6-well plates.

For use in gene transfer, retrovirus particles were prepared from the PT67 packaging cell line. In this regard, a pBabe puro Bmi1 (from Dr. G. P. Dimri, Evanston Northwestern Healthcare Research Institute, Feinberg School of Medicine, Northwestern University, Evanston, Ill. 60201, USA), constructed by inserting a human Bmi1 gene (NCBI accession No. L13689) into a pBabe puro vector and a pBabe neo Oct4 vector, constructed by inserting a human Oct4 gene (NCBI accession No. NM_002701) into a pBabe neo vector, were transfected into a PT67 packaging cell line (Clontech) with the aid of Turbofect (Fermentas), followed by drug selection with puromycine (3 μg/ml, BD bioscience) and neomycine (1000 μg/ml, BD biosciences). The PT67 packaging cell line allowed the production of high-titer viruses capable of infecting a broad range of mammalian host cells.

The expression of each gene was monitored with RT-PCR. When the cells were grown to 80% confluency, the supernatant was taken, filtered through a 0.45 μm filter (Millipore) to remove cell debris, and added to the cells in the presence of polybrene (6 μg/ml, sigma). The infection was repeated three times at regular intervals of 12 hrs.

Example 2

Reprogramming by Introduction of Oct4, Sox2 and Bmi1 Genes

Reprogramming was induced by introducing into mouse embryonic fibroblasts two genes Oct4 and Sox2 (2F) or three genes Oct4, Sox2 and Bmi1 (2F-Bmi1) and the results were compared.

After the retroviral transduction of Example 1 was performed, the cells were induced to undergo reprogramming under the culture conditions of mouse embryonic stem cells. To this end, the cells were subcultured in high-glucose DMEM supplemented with 15% FBS (Fetal bovine serum), 0.1 mM nonessential amino acid, 1% penicillin/streptomycin, 0.1 mM β-mercaptoethanol and 1000 unit/ml mouse LIF (leukemia inhibitory factor) in the presence of a feeder cell, with a passage every 2-3 days.

FIG. 1 shows reprogramming efficiencies upon introduction of Oct4 and Sox2 genes, and Oct4, Sox2 and Bmi1 genes. As seen in FIG. 1A, a far greater number of AP-positive colonies were generated from cells infected with retrovirus encoding Bmi1 gene plus two factor genes (Oct4 and Sox2) (2F-Bmi1) than with retrovirus encoding the two factor genes (2F). The established iPS cells were observed to have similar morphology to that of embryonic stem cells (FIG. 1B). AP staining was performed to examine whether the reprogrammed cells expressed markers characteristic of embryonic stem cells. Also, SSEA1, Oct4, Sox2, and Nanog were found to be expressed as measured by immunostaining (FIG. 1C). These data indicate that upon introduction of Oct4, Sox2 and Bmi1, somatic cells are allowed to undergo reprogramming, with Bmi1 playing an essential role in the reprogramming.

Example 3

Reprogramming of Mouse Embryonic Fibroblasts Into Neural Stem Cell-Like Cells by Bmi1 Gene Introduction When retroviral transduction was performed on mouse embryonic fibroblasts as in Example 1, the Bmi1 target genes $p16^{Ink4a}$ and $p19^{arf}$ were found to decrease in expression level as measured by a Western blotting assay, while Sox2 expression was increased (FIG. 2A).

When the Bmi1-transduced cells were cultured in a medium adapted for neural stem cells, they were observed to aggregate and change morphology to that of neurospheres (FIG. 2B). These cells were analyzed by AP staining and immunochemistry for Nestin and Sox2, markers typical of neural stem cells. Also, the Bmi1-transduced cells differentiated, like neural stem cells, into astrocytes, neurons and oligodendrocytes as measured by immunochemical staining for GFAP, Tuj1 and O4, which are respective markers typical thereof. Therefore, the introduction of Bmi1 gene induced mouse embryonic fibroblasts to undergo a reprogramming process into neural stem cell-like cells.

Example 4

Generation of Induced PS Cells by Introduction of Oct4 Bmi1 Genes

Figures 3, 3A:
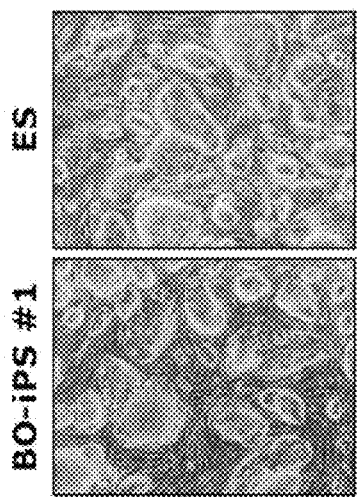
FIG. 3 shows the dedifferentiation of mouse embryonic fibroblasts into neural stem cells by retroviral transduction with Oct4 and Bmi1.
FIG. 3A shows mES cells and ESC-like morphology of BO-iPS established by introducing Bmi1 and Oct4 genes into mouse embryonic fibroblasts. Reprogramming efficiencies are given for a combination of Bmi1 and Oct4 and Oct4 alone (right panel). Oct4 in combination Bmi1 induced the mES cells to undergo a reprogramming process, successfully forming about 50 colonies whereas Oct4 alone could not.
Figure 3B:
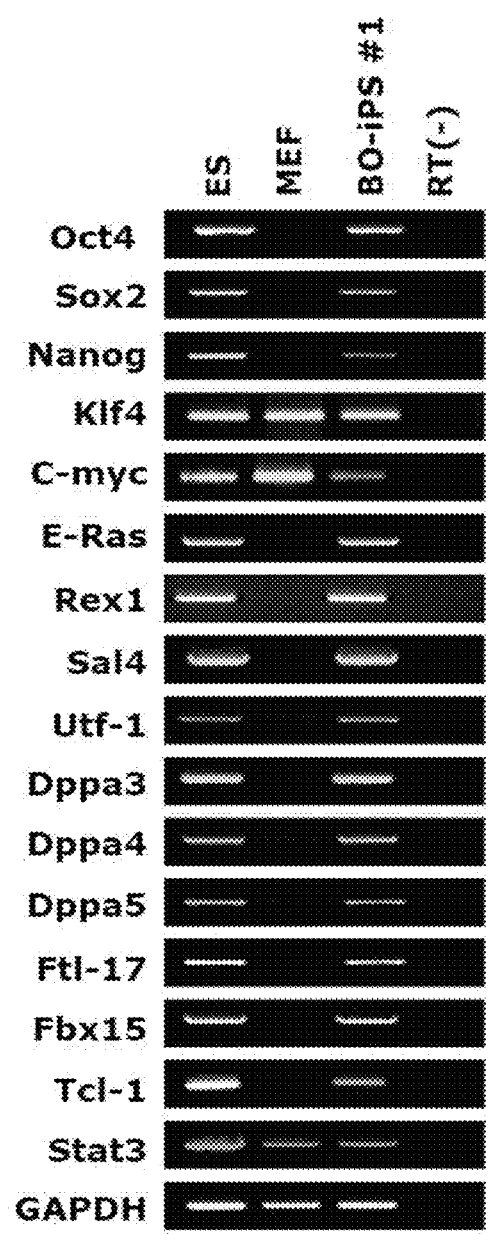
FIG. 3B shows the expression of important genes in induced stem cells in patterns similar to those in mES cells, as measured by RT-PCR.
Figure 3C:
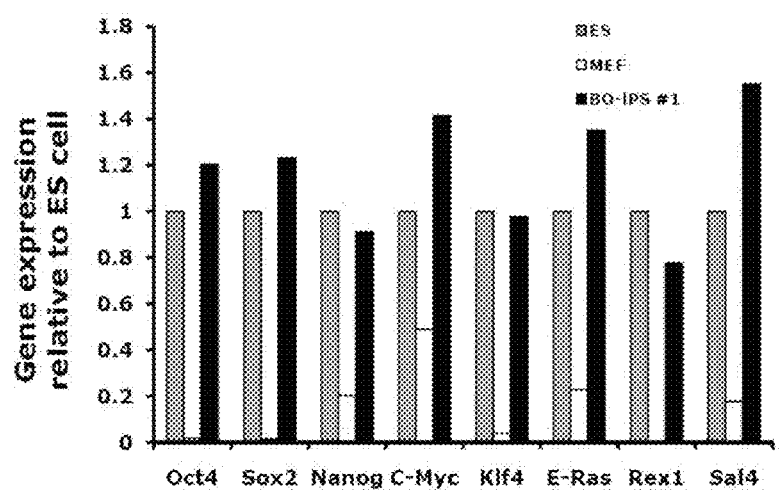
FIG. 3C shows similar expression patterns of important genes involved in the self-renewal of embryonic stem cells between induced stem cells and embryonic stem cells, as measured by real-time PCR.
Figure 3D:
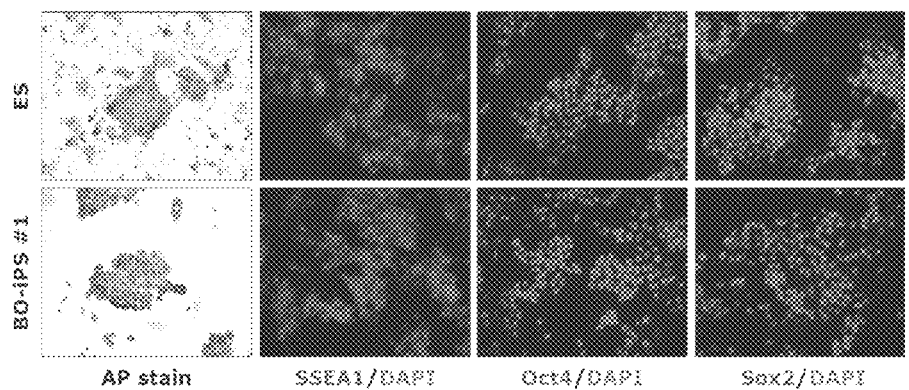
FIG. 3D shows the expression of markers specific for embryonic stem cells in the induced stem cells, as measured by immunocytochemistry.
Figure 3E:
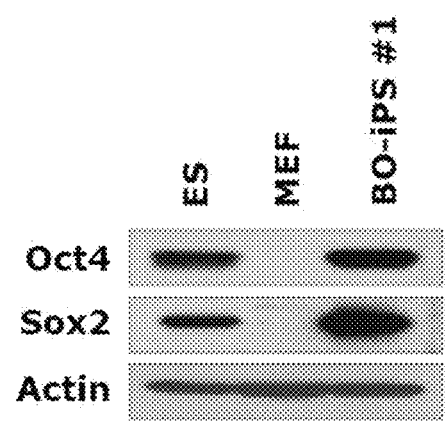
FIG. 3E shows the expression of Oct4 and Sox2 in the induced stem cells and the embryonic stem cells, as measured by Western blotting analysis.
Figure 3F:
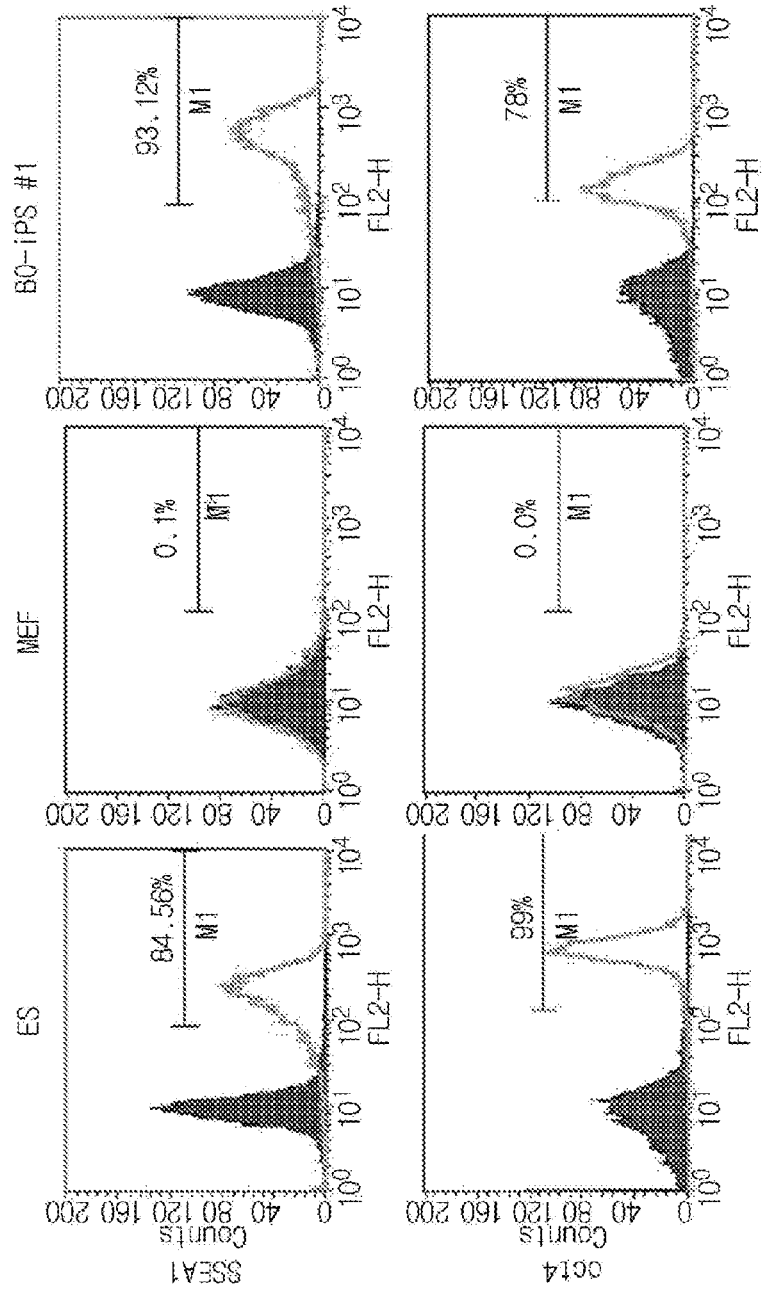
FIG. 3F shows the expression of SSEA1 and Oct4 in the induced stem cells to an extent similar to that of embryonic stem cells, but different from that of mouse embryonic fibroblasts, as measured by FACS analysis.

In consideration of the result that Bmi1-transduced mouse embryonic fibroblasts had an increased Sox2 expression level and were reprogrammed into neural stem cells, a reprogramming process was induced with Oct4 and Bmi1 genes alone. In contrast to Oct4 alone, which resulted in no colonies, the reprogramming with Bmi1 in combination with Oct4 allowed the appearance of about 50 colonies which had similar morphology to that of embryonic stem cells (FIG. 3A). These established iPS cells (BO-iPS) were found to express genes specific for embryonic stem cells as measured by RT-PCR and Real-time PCR (FIGS. 3B and 3C). Also, positive AP staining as well as SSEA1, Oct4 and Sox2 immunoreactivities was detected at BO-iPS (FIG. 3D). Proteins obtained from embryonic stem cells (ES), mouse embryonic fibroblasts (MEF) and induced stem cells (BO-iPS) were subjected to Western blotting to detect Oct4 and Sox2, markers characteristic of embryonic stem cells, and FACS analysis showed the expression of SSEA1 and Oct4 (FIGS. 3E and 3F). As is apparent from the data of FIG. 3, no exogenous Oct4 genes were expressed in BO-iPS. DNA PCR (genomic DNA PCR) revealed an Oct4 gene integrated into the genomic DNA of BO-iPS.

Example 5

Assay of Main Gene Promoters for Methylation in BO-iPS and ES

Figures 4, 4A:
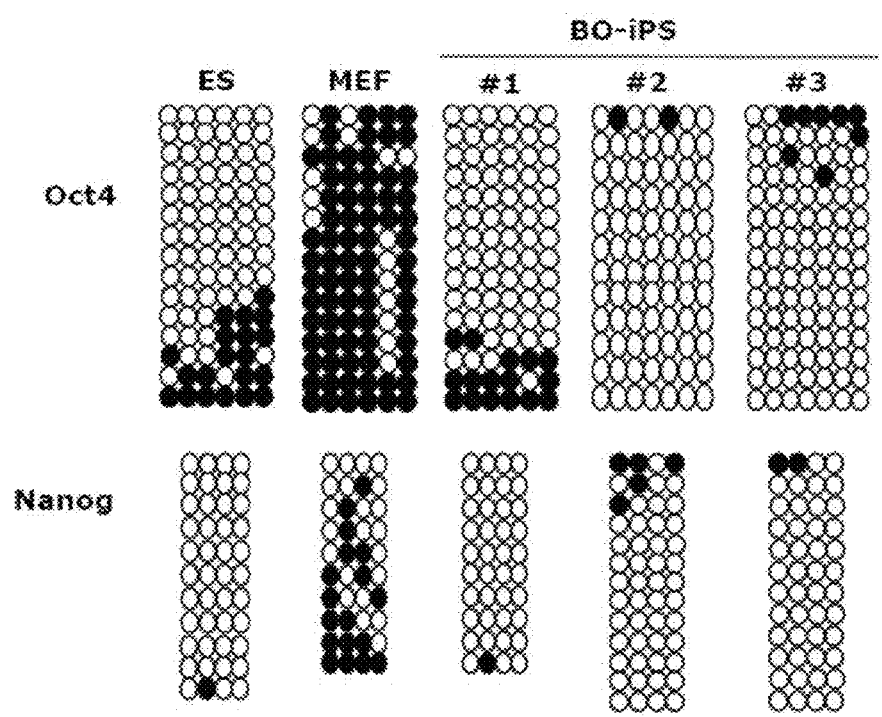
FIG. 4 shows epigenetic variations of the embryonic stem cell-like cells of the present invention.
FIG. 4A showing the methylation of the promoter regions of Oct4 and Nanog, both involved in the self-renewal of embryonic stem cells, as measured by bisulfite sequencing. The promoter regions are, for the most part, methylated in mouse embryonic fibroblasts, but demethylated in the induced stem cells like embryonic stem cells. This is true of each clone.
Figure 4B:
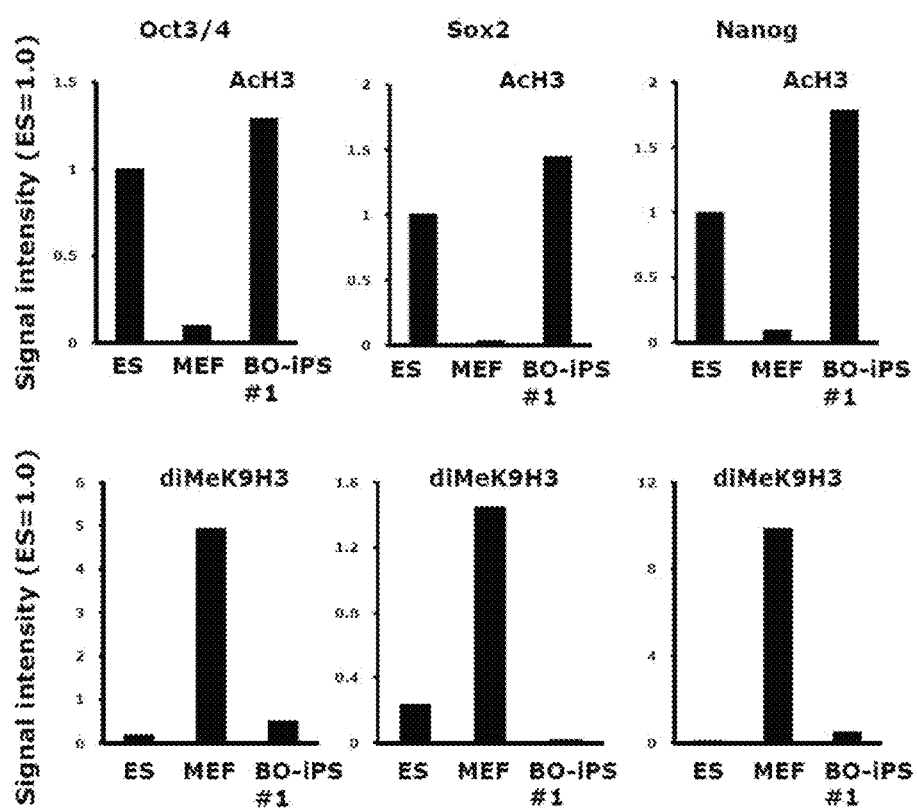
FIG. 4B shows the chromatin immunoprecipitation analysis for acetylation and methylation of histon H3, as confirmed by real-time PCR. The Oct4, Sox2, and Nanog promoters increased the acetylation of histone H3 (AcH3) in BO-iPS cells as in mES, and decreased the demethylation of lysine 9 of histone H3 in mouse embryonic fibroblasts.

Promoters of the genes essential for the self-renewal of embryonic stem cells were assayed in induced stem cells, embryonic stem cells and mouse embryonic fibroblasts. Bisulfite sequencing was performed to examine the methylation status of Oct4 and Nanog promoter regions. They were, for the most part, methylated in mouse embryonic fibroblasts, but demethylated in the induced stem cells like embryonic stem cells. These results were true of the homogenous clones (FIG. 4A). Chromatin immunoprecipitation analyses showed that the Oct4, Sox2, and Nanog promoters had increased the acetylation of histone H3 in ES and BO-iPS and the demethylation at position K9 in MEF (FIG. 4B).

Example 6

DNA Microarray Assay for Gene Expression in Embryonic Stem Cells and Induced Stem Cells Gene expression profiles in embryonic stem cells, mouse embryonic fibroblasts and induced stem cells were examined by microarray assay, and expressed in scatter plots, showing that that the induced stem cells were similar in expression profile of the genes essential for the self-renewal of embryonic stem cells to that of embryonic stem cells, but different from mouse embryonic fibroblasts.

Figure 5:
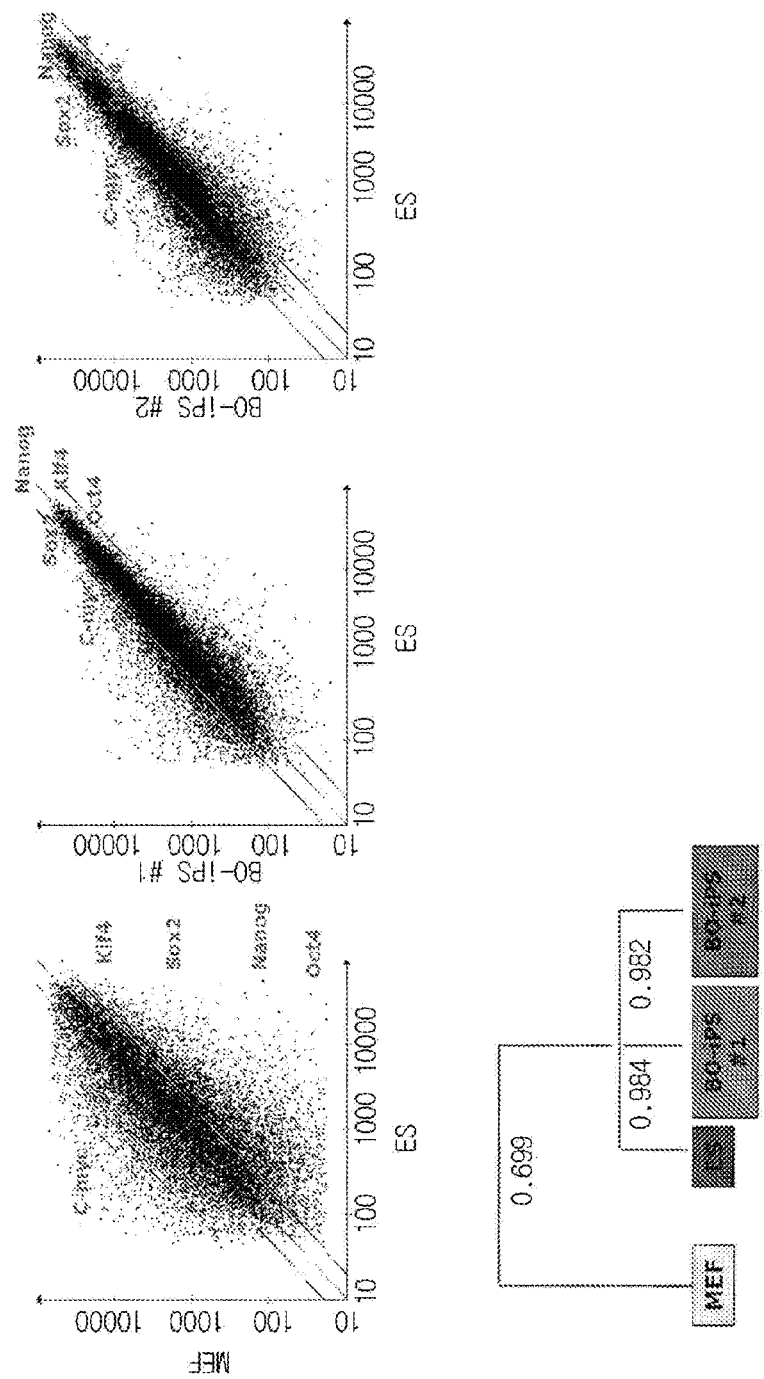
FIG. 5 shows the global gene expression profiles obtained by DNA microarray analysis. The Pearson correlation analysis of mES, MEF and iPS cells shows that iPS cells are highly correlated with mES cells, with a correlation coefficient of 0.98 therebetween and poorly correlated with MEF cells, with a correlation coefficient of 0.69 therebetween (lower panel). Scatter plots of the global gene expression profiles shows that BO-iPS cells and their clones are quite different from MEF cells, but are similar to mES cells. Also, the expression levels of the most genes are within the range of 2-fold changes, indicating a similarity in gene expression pattern between BO-iPS cells and mES cells.

Homogenous clones also exhibited similar patterns between the induced stem cells and the embryonic stem cells. High correlation between the induced stem cells and the embryonic stem cells was confirmed by a Pearson correlation coefficient of 0.98 (FIG. 5).

Example 7

Differentiation Potential and Chimera Formation of BO-iPS

Figure 6C:
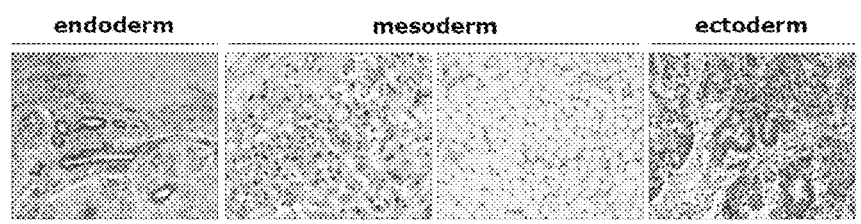
FIG. 6C shows the induction of in-vivo differentiation into all three germ layers. iPS cells were injected under the kidney capsule into Balb/c nude mice, 8-10 weeks after which the mice developed teratomas which were prepared for H&E staining.

BO-iPS cells were examined for differentiation potential in vitro by an embryonic body assay. RT-PCR showed that BO-iPS expressed genes accounting for the three germ layers in a pattern similar to that of ES (FIG. 6A). Embryonic bodies derived from BO-iPS cells were found to differentiate into typical cells corresponding to the three germ layers as measured by staining with respective characteristic markers. In this context, immunochemistry were performed with Tuj1, bry, SMA, and GATA4, indicating that BO-iPS cells have the same in vitro differentiation potential as ES cells (FIG. 6B).

Figure 6D:
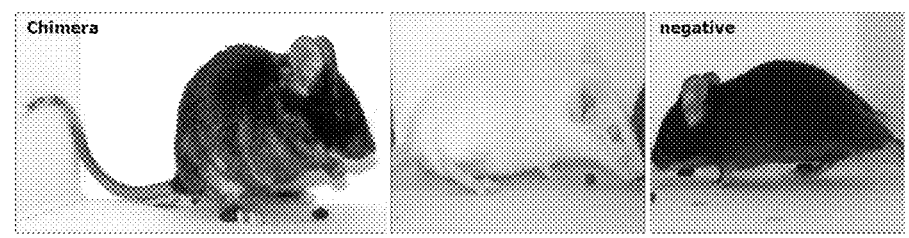
FIG. 6D shows chimera formation when BO-iPS cells are injected into blastocysts.

To investigate the differentiation potential of BO-iPS cells in vivo, they were assayed for teratoma formation. $1\times10^6$ cells were centrifuged at 8000 rpm for 5 min and the pellet thus obtained was cultured for 24 hrs in a proliferation medium for embryonic stem cells, followed by injecting the cells under the kidney capsule into the dorsal flank of 6-week-old Balb/c nude mice. Eight to ten weeks later, the kidney was excised, embedded in paraffin, and processed for H&E staining. The results showed the differentiation of BO-iPS cells into cells corresponding to the three germ lines. The cells were injected into the blastocysts of C57/BL6. The injected blastocysts were transferred into a surrogate female. Chimeric mice were born at F1. Chimera formation was evident by comparing the surrogate mice with C57/BL6 mice (FIG. 6D). These results demonstrated that BO-iPS cells have properties similar to those of ES cells.

Example 8

Figure 7C:
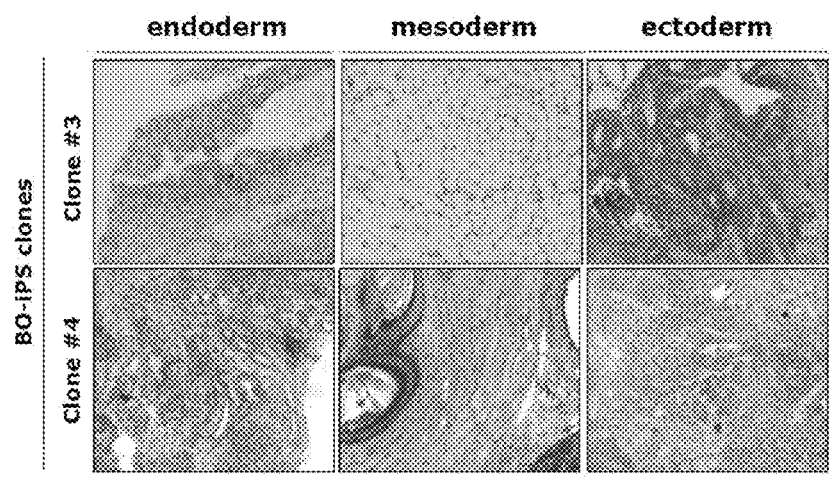
FIG. 7C shows in vivo teratoma formation of the clones after they are injected under the kidney capsule into Balb/c nude mice, 8-10 weeks after which the three germ layers are detected.

Examination of Whether a Homogeneous Population Of BO-iPS Cells has Similar Properties to Those of ES Cells To investigate whether a homogenous population of BO-iPS cells showed the same properties as did ES cells, single cell clones were made. 5 clones of BO-iPS were assayed for the expression of genes essential for ES cells. A expression profile similar to the total was detected therebetween as assayed by RT-PCR (FIG. 7A). Positive AP staining as well as SSEA1, Oct4 and Sox2 immunoreactivities were detected at the clones (FIG. 7B). In addition, the teratoma formation of the clones was identified by H&E staining (FIG. 7C).

Figure 8:
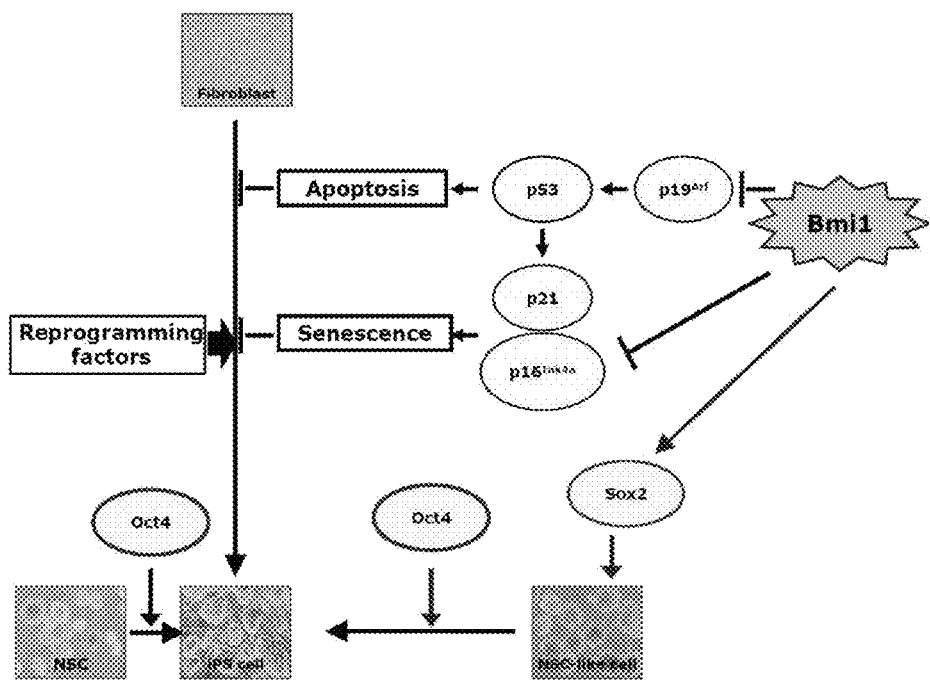
FIG. 8 is a schematic diagram, showing a novel process of reprogramming fibroblasts to generate induced pluripotent stem cells using Oct4 and Bmi1.

FIG. 8 is a schematic diagram, designed on the basis of the data demonstrating the hypothesis for this invention, showing a novel process of reprogramming somatic cells to generate induced pluripotent stem cells. The introduction of the novel reprogramming factor Bmi1 in combination with Oct4 gene allows somatic cells to undergo a reprogramming process. Further, the employment of an upstream regulator, which replaces Bmi1, enjoys the advantage of reducing the number of reprogramming factors and allows insight into a technique for generating induced pluripotent stem cells without introducing genes.

Example 9

Bmi1 Expression by Treatment with Shh or Shh Analog, and Oct4 Gene Introduction

Figure 9A:
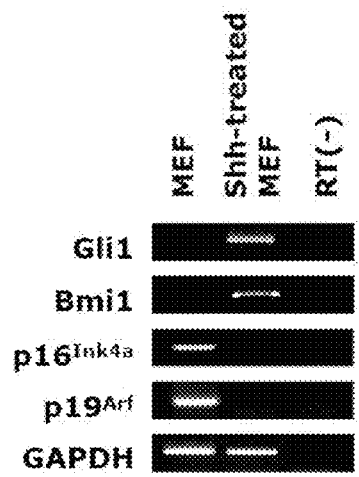
FIGS. 9A to 9D show the induction of Bmi1 by Shh (sonic hedgehog) treatment.
Figure 14A:
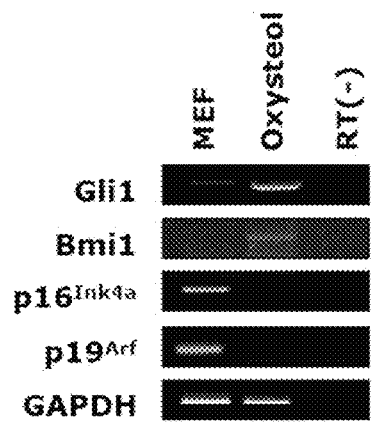
FIGS. 14A to 14D show the induction of Bmi1 by treatment with hydroxycholesterol (oxysterol), a Shh analog.
Figure 22A:
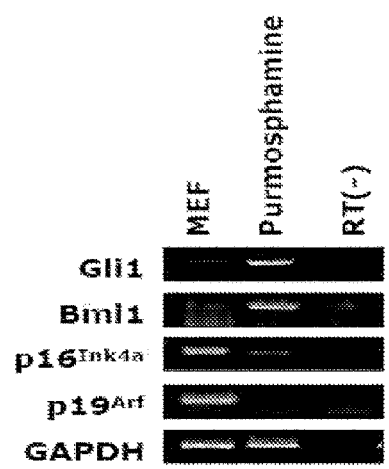
FIGS. 22A to 22D show the induction of Bmi1 by treatment with the Shh analog purmorphamine.

The fibroblasts prepared in Example 1 were examined for Bmi1 expression when they were treated with Shh or an analog thereof, such as oxysterol or purmorphamine. FIGS. 9A, 14A and 22A are RT-PCR results showing the effect of Shh (Sonic hedgehog), known as an upstream regulator of Bmi1, or its analogs on the expression of genes downstream thereof. Treatment with 500 ng/ml of Shh, 0.1 μM and 0.5 μM of hydroxycholesterol (Sigma, 25-hydroxycholesterol, H1015), or 0.5 μM or 1 μM of purmorphamine (Calbiochem cat. no. 540220) in neural stem cell-culturing conditions (DMEM/F12+B27+N2+1% penicillin/streptomycin+20 ng/ml bFGF+20 ng/ml EGF) resulted in upregulation of Gli1 and Bmi1 and downregulation of the Bmi1 target genes $p16^{Ink4a}$ and $p19^{Arf}$.

Figure 9B:
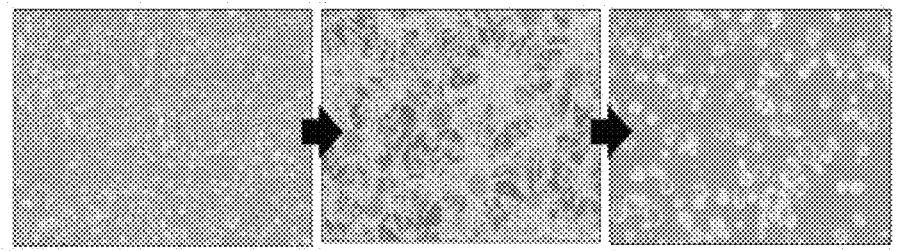
Figure 9C:
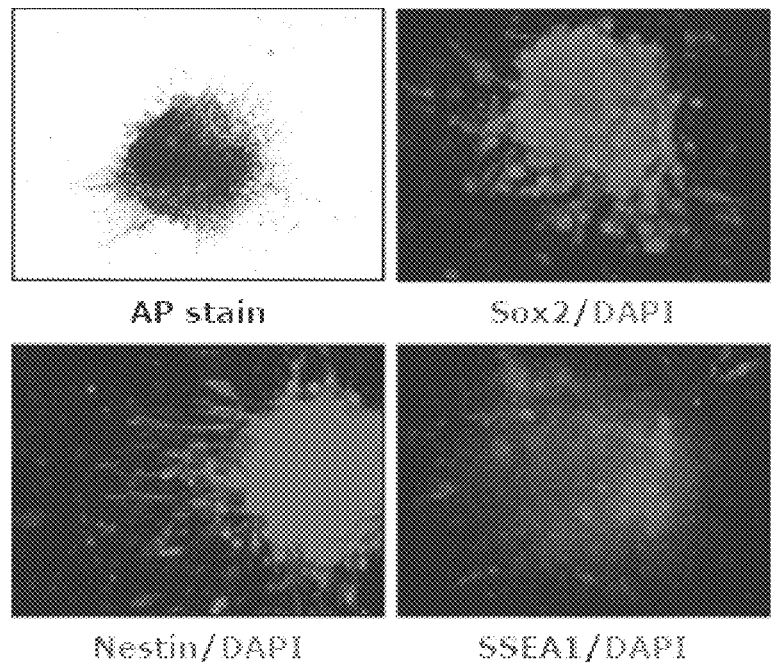
Figure 14B:
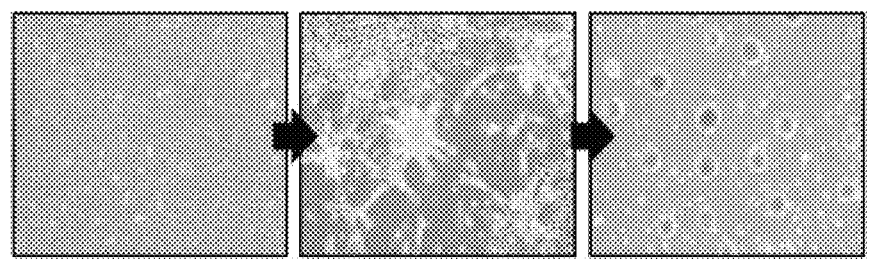
Figure 14C:
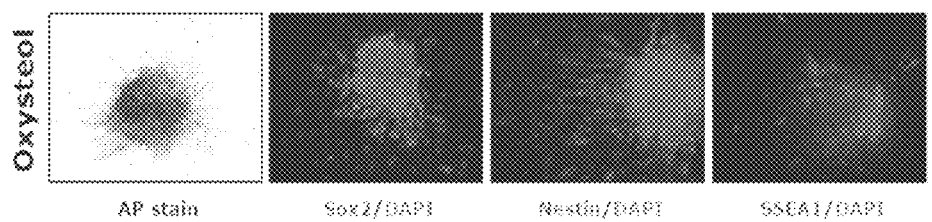
Figure 22B:
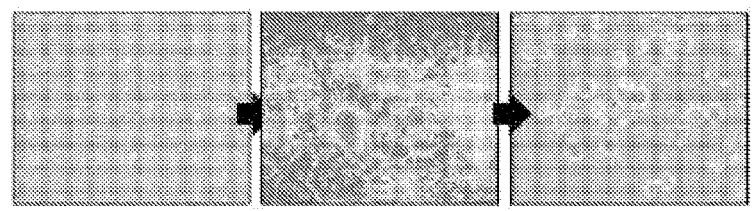
Figure 22C:
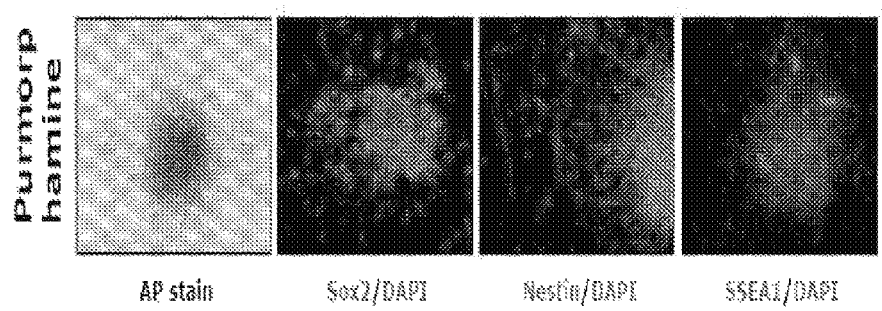

Also, the cells were observed to aggregate and change their morphology to that of neurons (FIGS. 9B, 14B and 22B). The induced neural stem cell-like cells were positively analyzed by AP staining and immunochemistry for SSEA1, Nestin and Sox2 (FIGS. 9C, 14C and 22C). Therefore, Shh-treated cells showed properties similar to those of Bmi1-transduced cells.

For use in the introduction of an Oct4 gene into the fibroblasts treated with Shh or its analog hydroxycholesterol or purmorphamine, retrovirus particles were prepared from the PT67 packaging cell line. In this regard, a pBabe neo Oct4 vector, constructed by inserting a human Oct4 gene (NCBI accession No. NM_002701) into a pBabe neo vector, was transfected into a PT67 packaging cell line (Clontech) with the aid of Turbofect (Fermentas), followed by drug selection with neomycine (1000 μg/ml, BD biosciences). The PT67 packaging cell line allowed the production of high-titer viruses capable of infecting a broad range of mammalian host cells.

The expression of Oct4 was monitored with RT-PCR. When the cells were grown to 80% confluency, the supernatant was taken, filtered through a 0.45 μm filter (Millipore) to remove cell debris, and added to the cells in the presence of polybrene (6 μg/ml, sigma). The infection was repeated three times at regular intervals of 16 hrs.

Figure 9D:
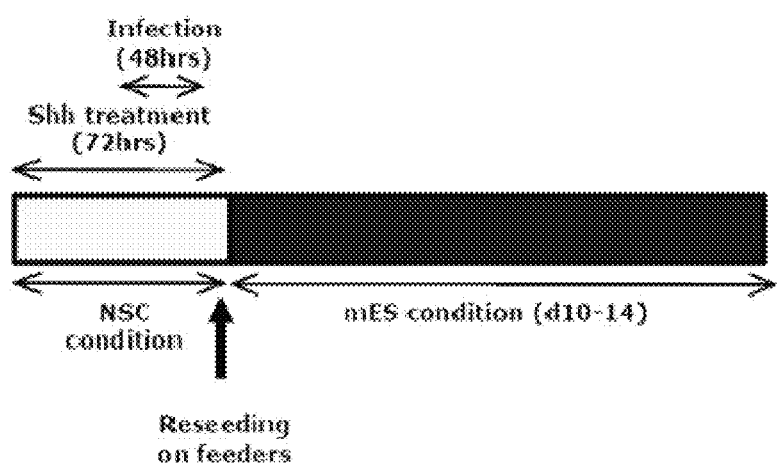
Figure 14D:
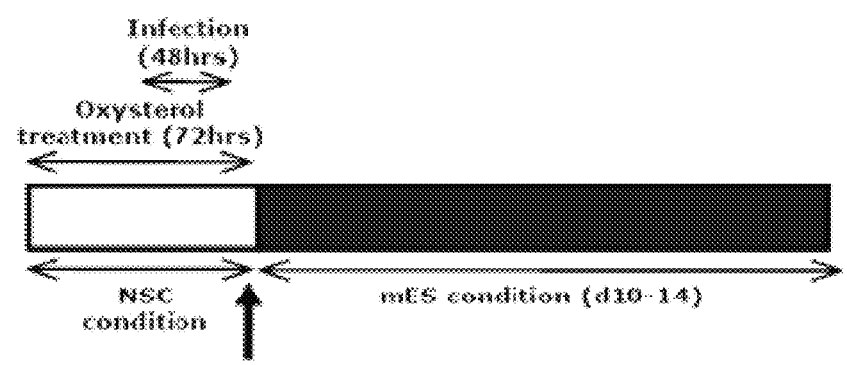
Figure 22D:
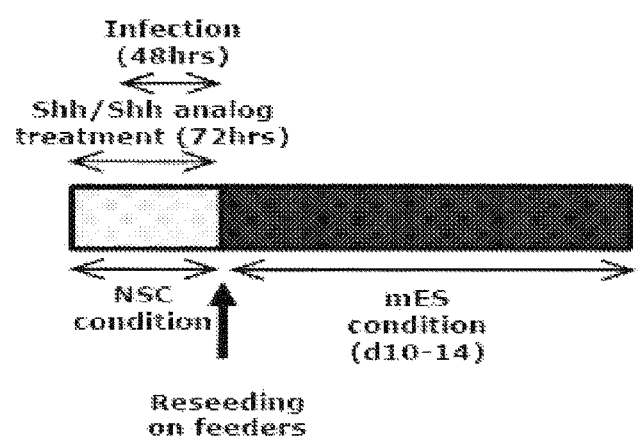

Using the retroviral system, the Oct4 gene was introduced three times at regular intervals of 16 hrs for a total period of hrs into fibroblasts while they were treated with Shh, hydroxycholesterol or purmorphamine. This treatment was continued for a total period of 72 hrs. During the treatment, the neural stem cell-culturing conditions were maintained. Thereafter, the conditions were changed into one for embryonic stem cells to induce the reprogramming process. FIGS. 9D, 14D and 22D are schematic diagrams showing reprogramming protocols for treatment with Shh, hydroxycholesterol or purmorphamine, transduction of Oct4 gene, and culturing in a condition for embryonic stem cells. This protocol was based on conventional protocols applicable to gene introduction and chemical treatment with Oct4 and Sox2, but advanced over the conventional protocols as described herein. After the reprogramming process was conducted for 10-14 days, colonies appeared with the same morphology as ES cells.

Example 10

Establishment of iPS Cells by Oct4 Introduction while Treatment with Shh or its Analog According to the protocol suggested in Example 9, iPS cells were established by the retroviral transduction of Oct4 while treatment with Shh or its analog hydroxycholesterol or permorphamine and then by culturing under the conditions used for mouse embryonic stem cells. These conditions were such that the cells were cultured in high-glucose DMEM supplemented with 15% FBS (Fetal bovine serum), 0.1 mM nonessential amino acid, 1% penicillin/streptomycin, 0.1 mM β-mercaptoethanol and 1000 unit/ml mouse LIF (leukemia inhibitory factor) in the presence of a feeder cell, with a passage every 2-3 days. After culturing for 10-14 days, colonies started to appear with a morphology similar to that of embryonic stem cells. The induced stem cells thus established were named SO-iPS, OO-iPS, and PO-iPS, respectively.

Figure 10A:
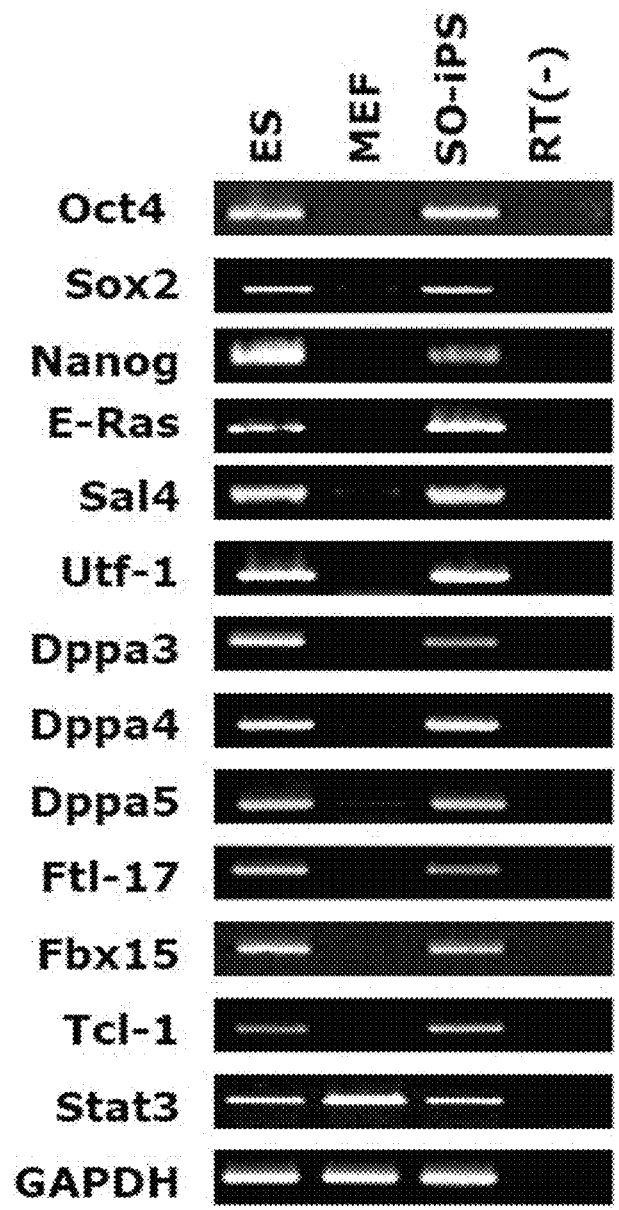
FIGS. 10A to 10E show the comparison of iPS cells generated by the introduction of Oct4 gene under the Shh treatment, with ES cells.
Figure 10B:
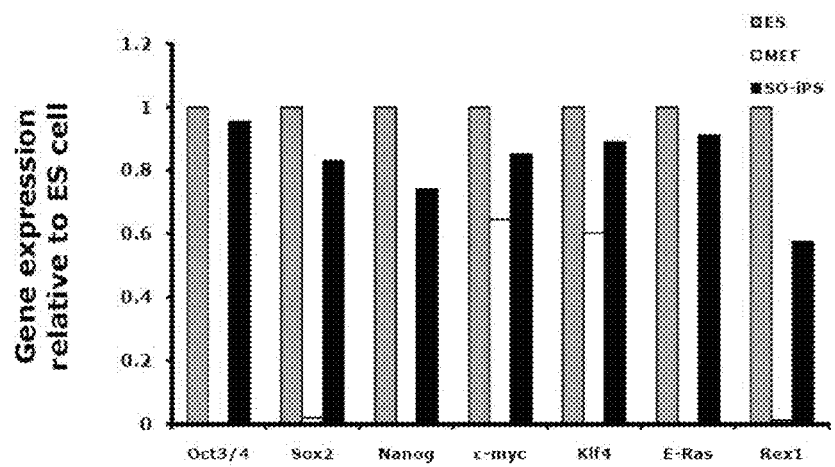
Figure 10C:
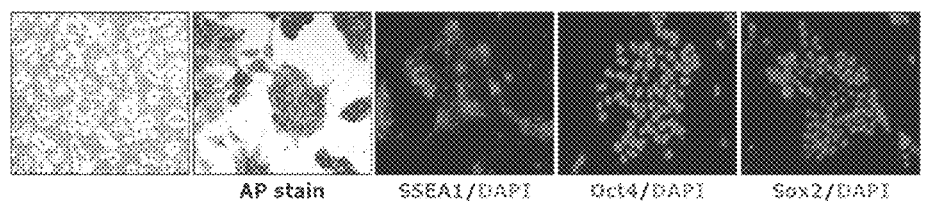
Figure 10D:
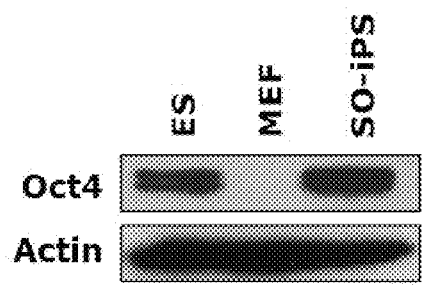
Figure 10E:
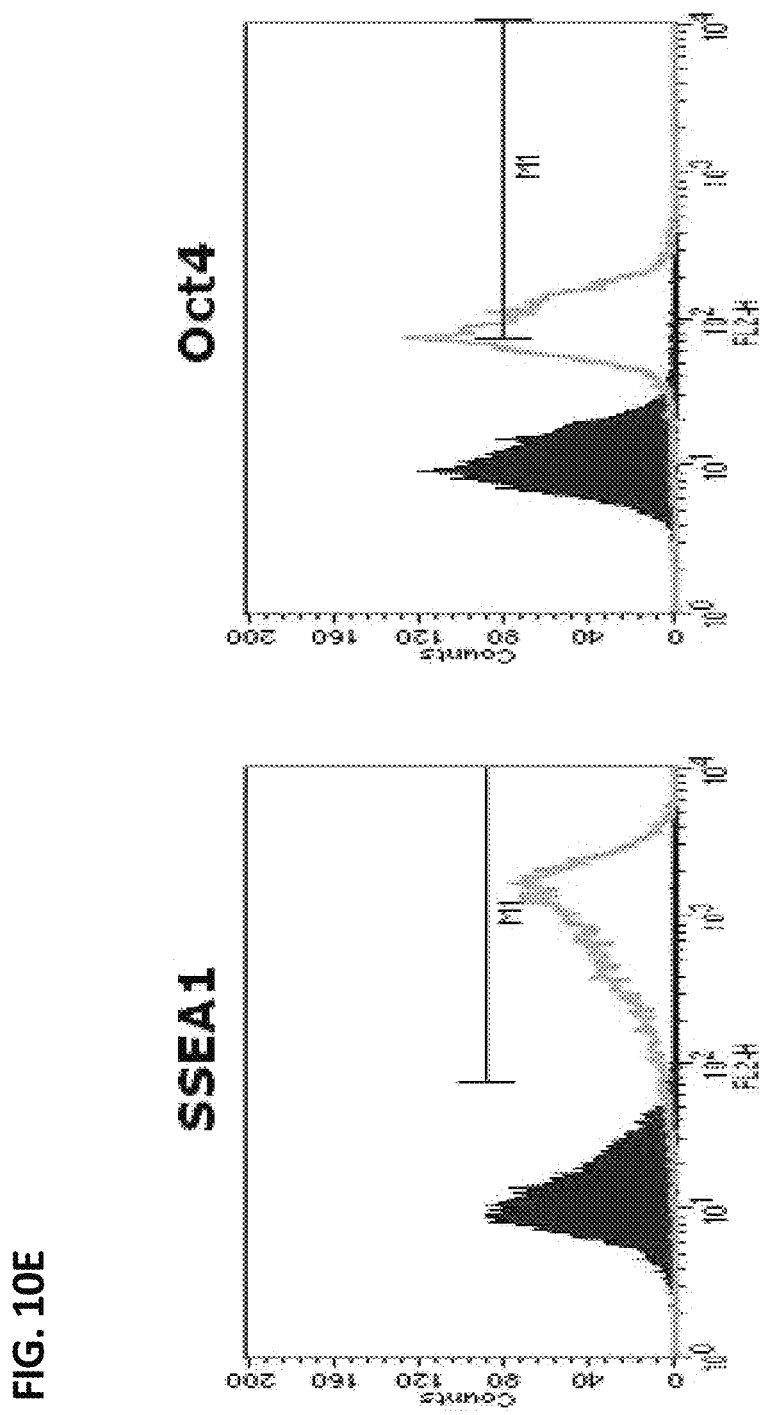

SO-iPS cells were analyzed and compared to embryonic stem cells. RT-PCR for genes essential for embryonic stem cells showed that there was a similarity in the expression profiles of the genes between SO-iPS and ES cells (FIG. 10A). SO-iPS cells were also found to have the same expression patterns of genes essential for self-renewal as ES cells as quantitatively measured by real-time PCR (FIG. 10B). Morphologies similar to those of ES cells were observed in SO-iPS cells. Positive AP staining was detected. Expression patterns of Oct4, SSEA1 and Sox2 were also similar to those of ES cells, as measured by immunochemical staining (FIG. 10C). Western blotting analysis indicated the expression of Oct4 as in ES cells (FIG. 10D). FACS analysis showed that Oct4 and SSEA1 were expressed in large quantities as they are in ES cells (FIG. 10E).

Figure 15A:
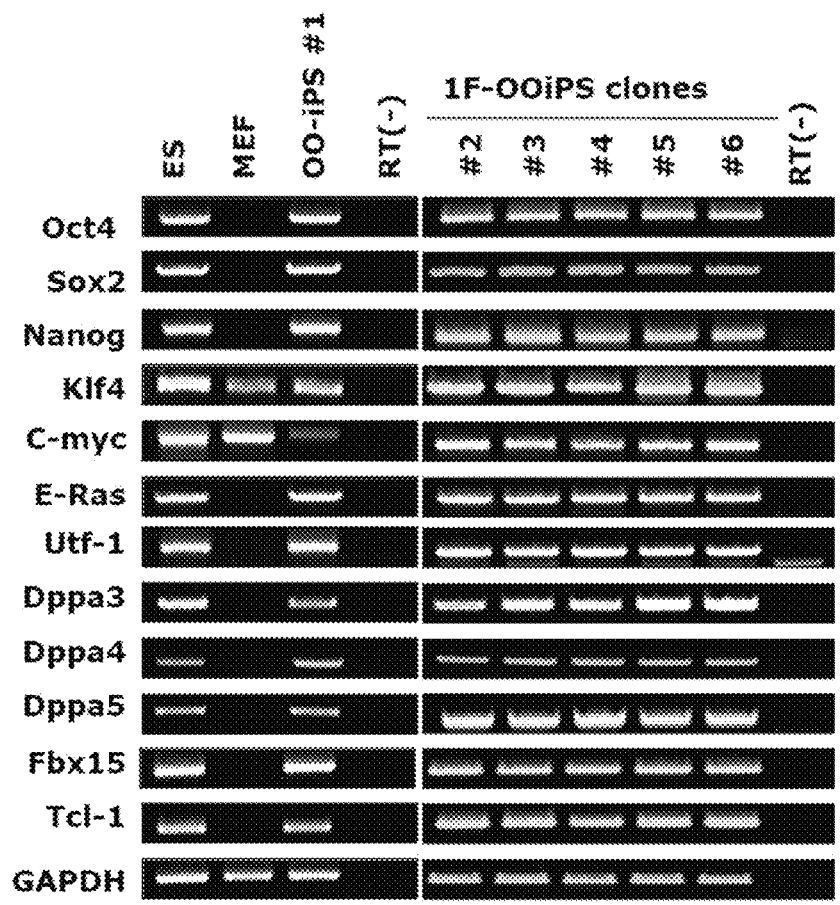
FIGS. 15A to 15D show the comparison of iPS cells generated by the introduction of Oct4 gene under the oxysterol treatment, with ES cells.
Figure 15B:
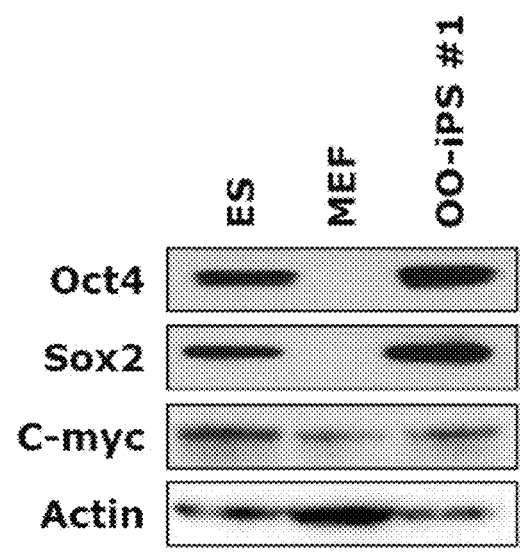
Figure 15C:
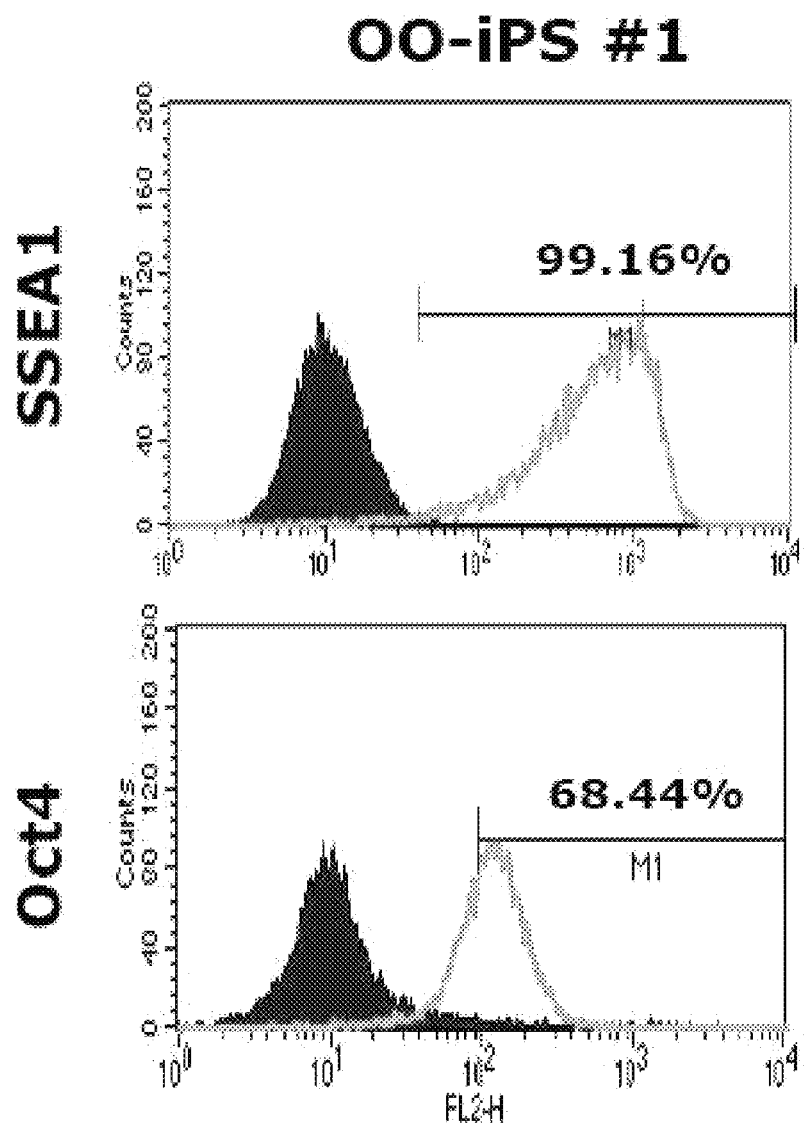
Figure 15D:
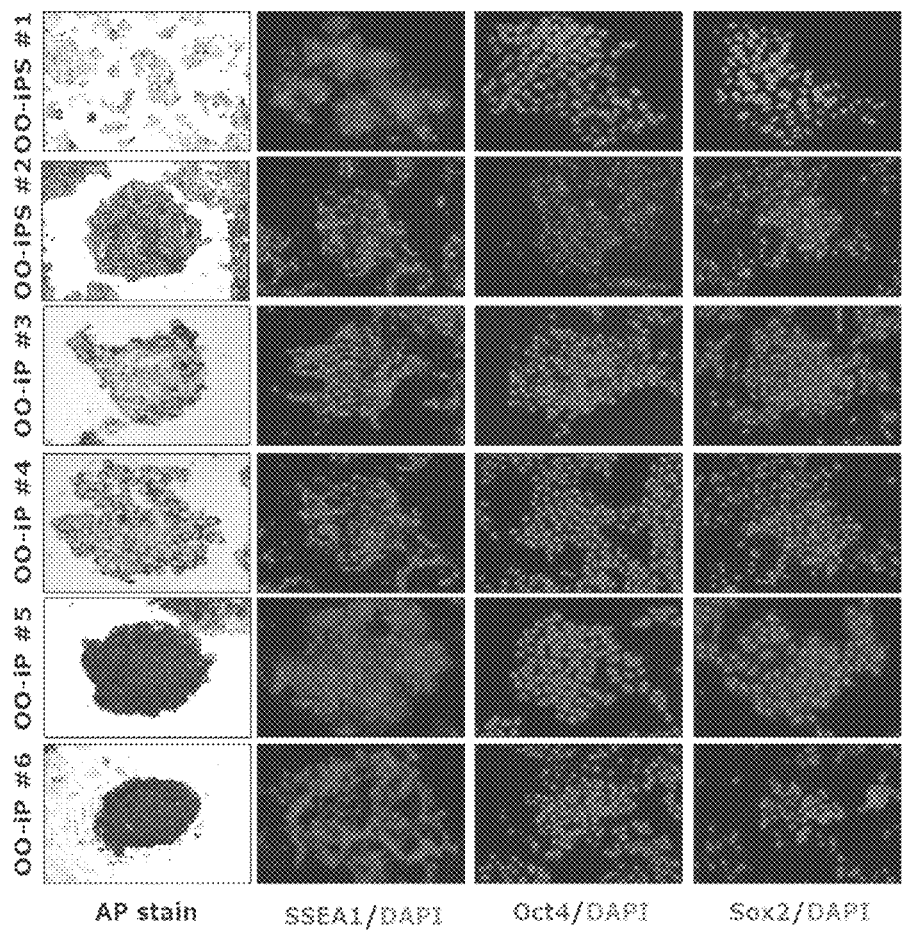

OO-iPS cells were analyzed to be compared with embryonic stem cells. RT-PCR for genes essential for embryonic stem cells showed that there was a similarity in the expression profiles of the genes between OO-iPS cells and ES cells (FIG. 15A). This was true of the homogeneous clones of the induced stem cells (FIG. 15A). Western blotting analysis detected the expression of Oct4 and Sox2 (FIG. 15B). Also, FACS data showed that both SSEA1 and Oct4 were expressed to a degree similar to that in ES cells (FIG. 15C). Morphologies similar to those of ES cells were observed in OO-iPS cells. Positive AP staining was detected. Expression patterns of Oct4, SSEA1 and Sox2 were also similar to those of ES cells, as measured by immunochemical staining. This was true of the clones of the induced stem cells (FIG. 15D).

Figure 23A:
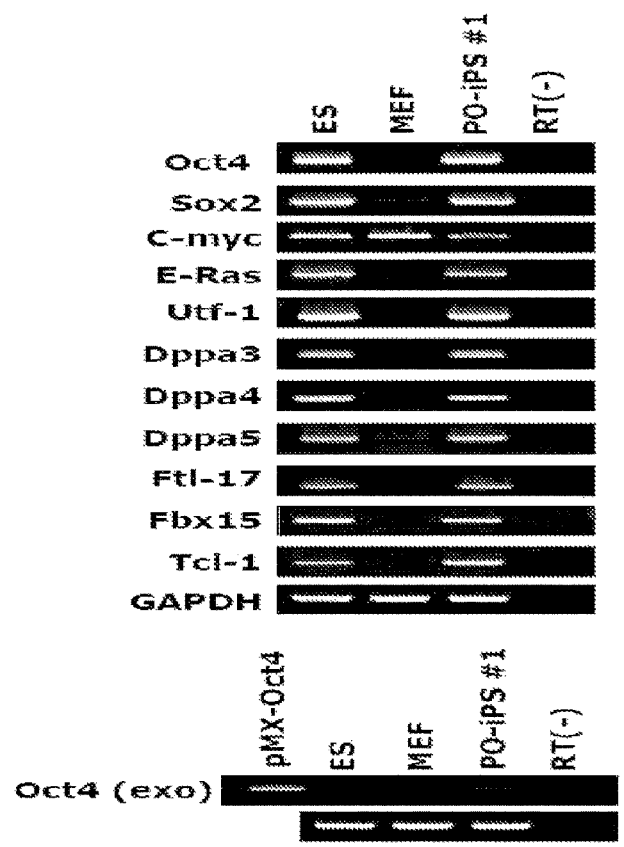
FIGS. 23A to 23E show the comparison of the induced stem cells generated by the introduction of Oct4 gene under the purmorphamine treatment, with embryonic stem cells.
Figure 23B:
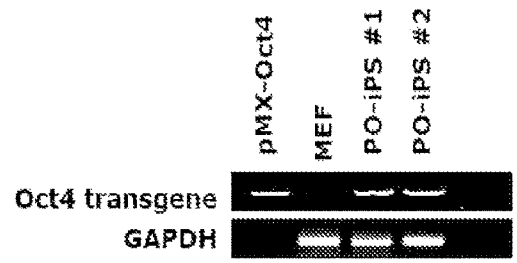
Figure 23C:
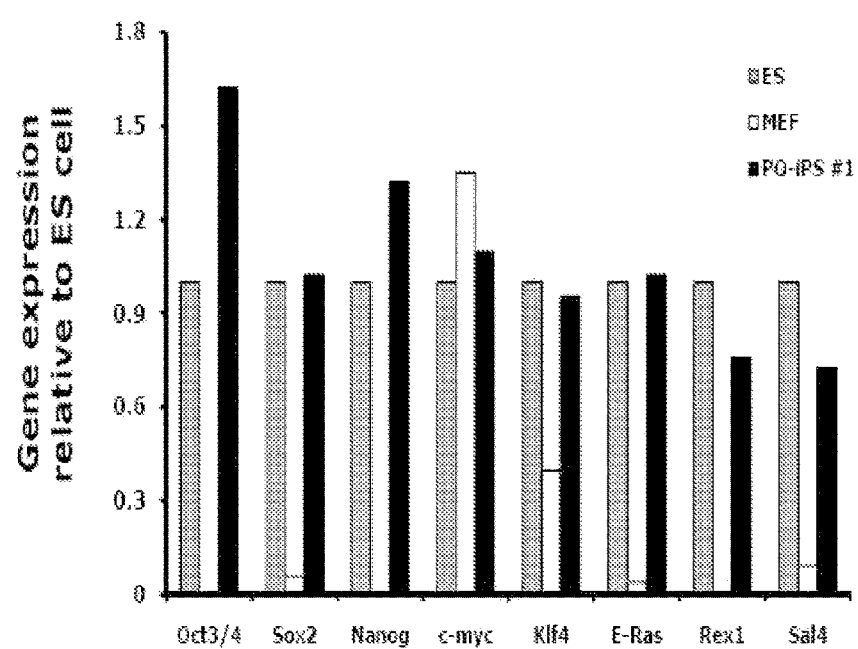
Figure 23D:
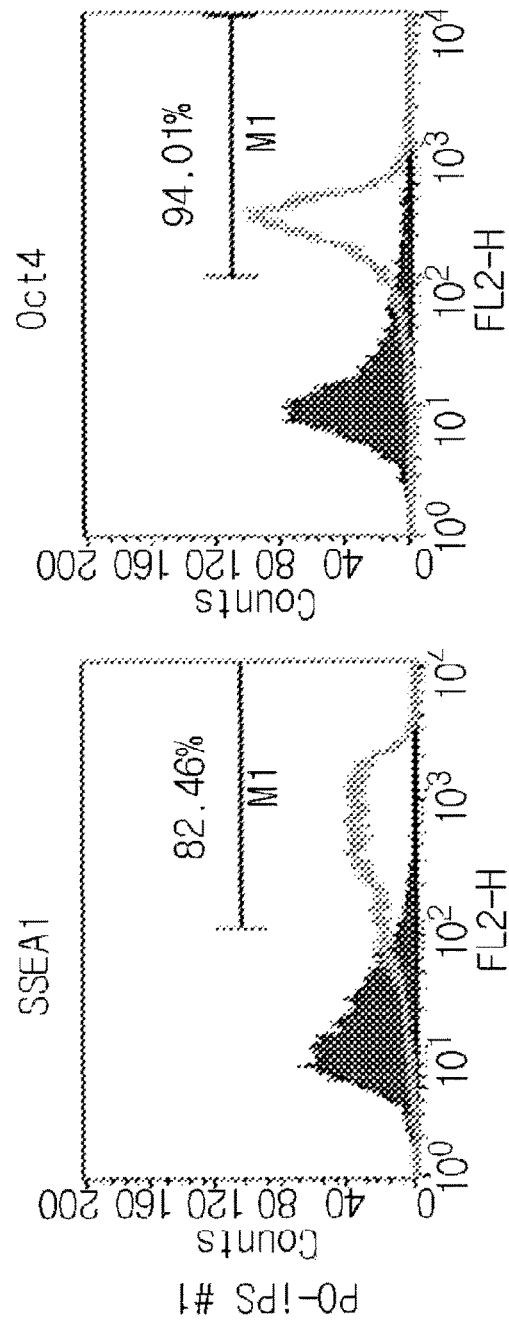
Figure 23E:
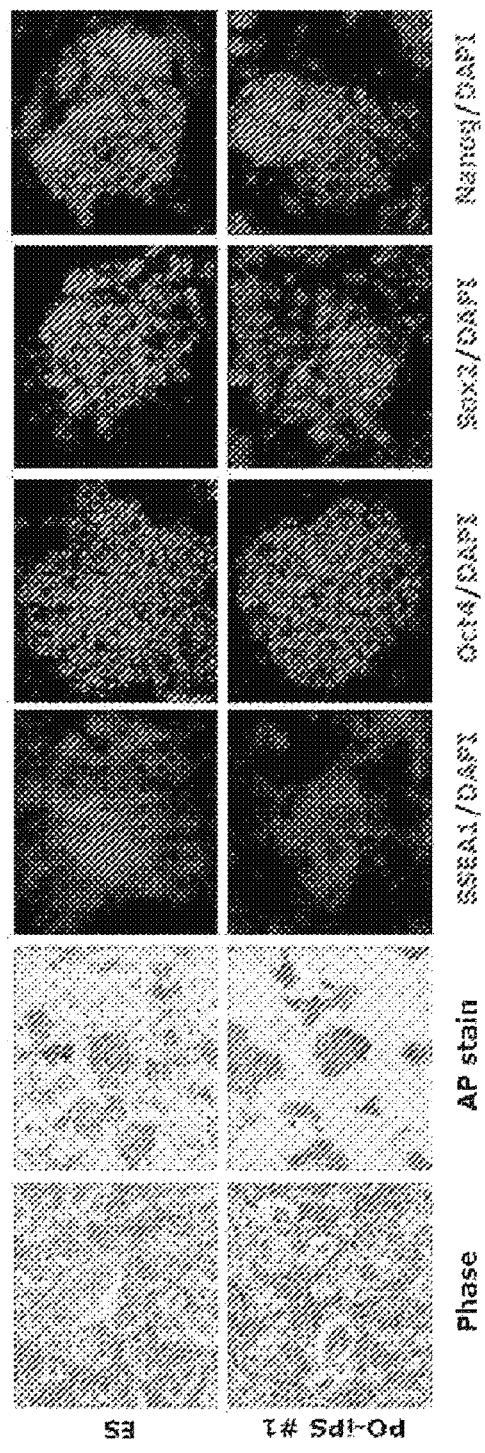

PO-iPS cells were analyzed and compared with embryonic stem cells. RT-PCR for genes essential for embryonic stem cells showed that there was a similarity in the expression profiles of the genes between PO-iPS cells and ES cells (FIG. 23A). The exogenous Oct4 gene was silenced in the induced stem cells. DNA PCR (genomic DNA PCR) revealed an Oct4 gene integrated into the genomic DNA of PO-iPS (FIG. 23B). PO-iPS cells were also found to have the same expression patterns of genes essential for self-renewal as ES cells have as quantitatively measured by real-time PCR (FIG. 23C). Also, FACS data showed that both SSEA1 and Oct4 were expressed to a degree similar to that found in ES cells (FIG. 23D). Morphologies similar to those of ES cells were observed in PO-iPS cells. Positive AP staining was detected. Expression patterns of Oct4, SSEA, Sox2 and Nanog were also similar to those of ES cells, as measured by immunochemical staining (FIG. 23E).

Example 11

Examination of SO-iPS, OO-iPS and PO-iPS for Epigenics

Figure 11A:
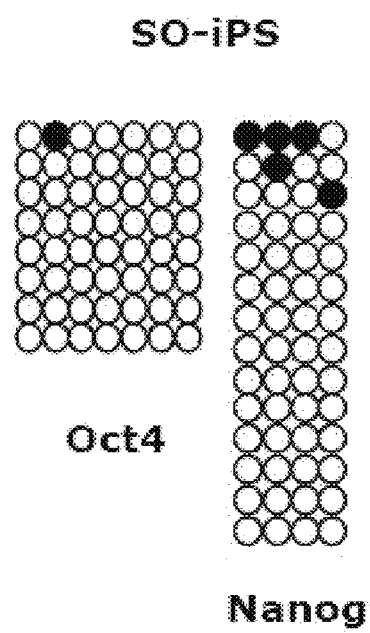
FIGS. 11A and 11B show the comparison of epigenetics between the embryonic stem cell-like cells of the present invention and embryonic stem cells.
Figure 11B:
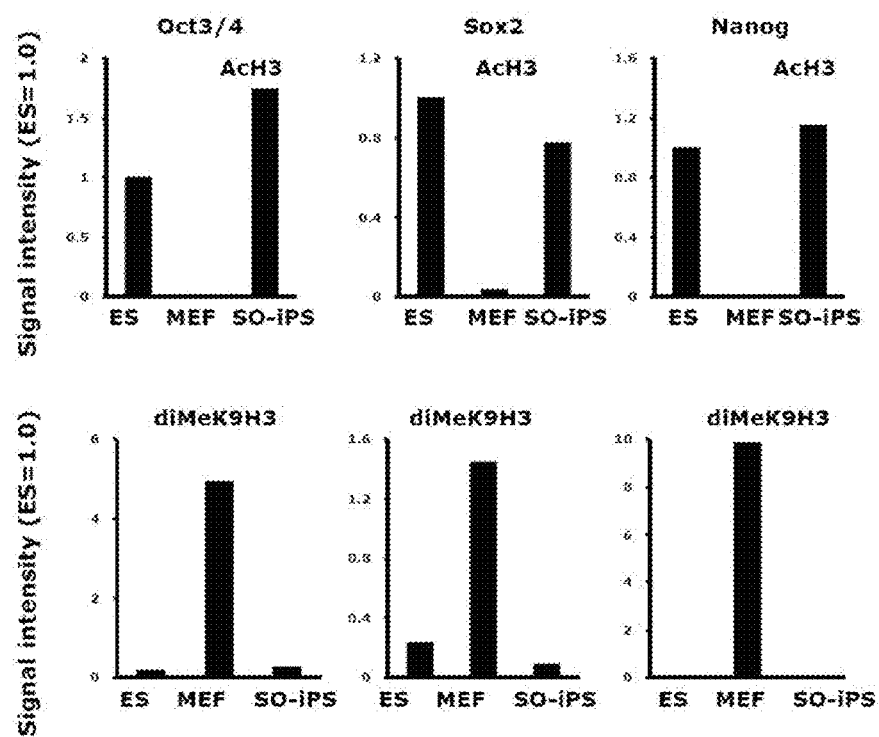
Figure 16A:
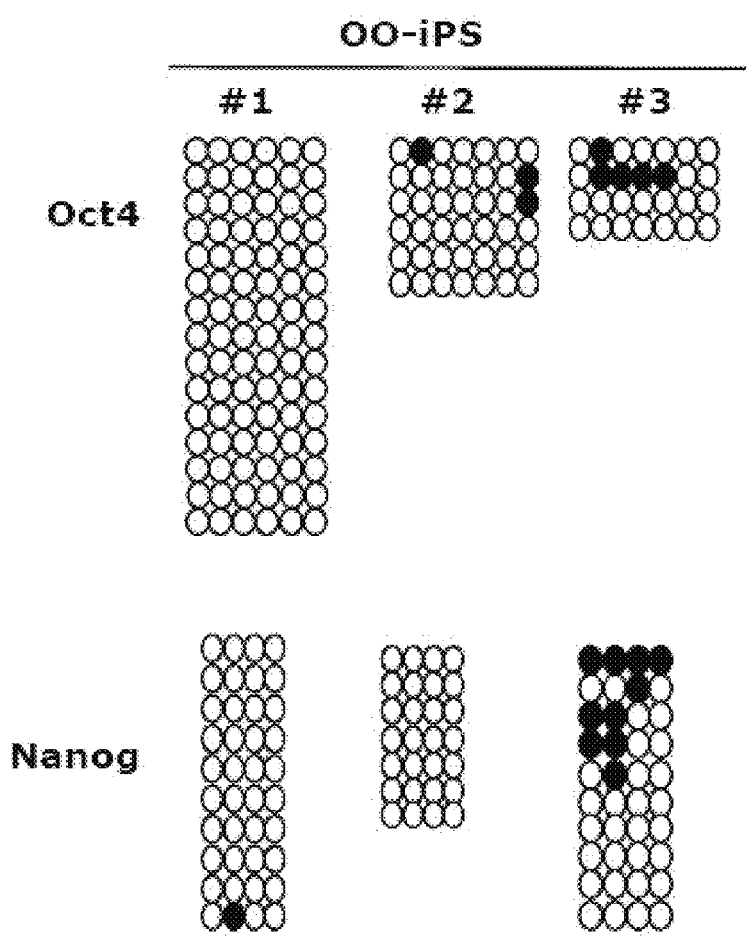
FIGS. 16A and 16B show the comparison of epigenetics between the embryonic stem cell-like cells of the present invention and embryonic stem cells.
Figure 16B:
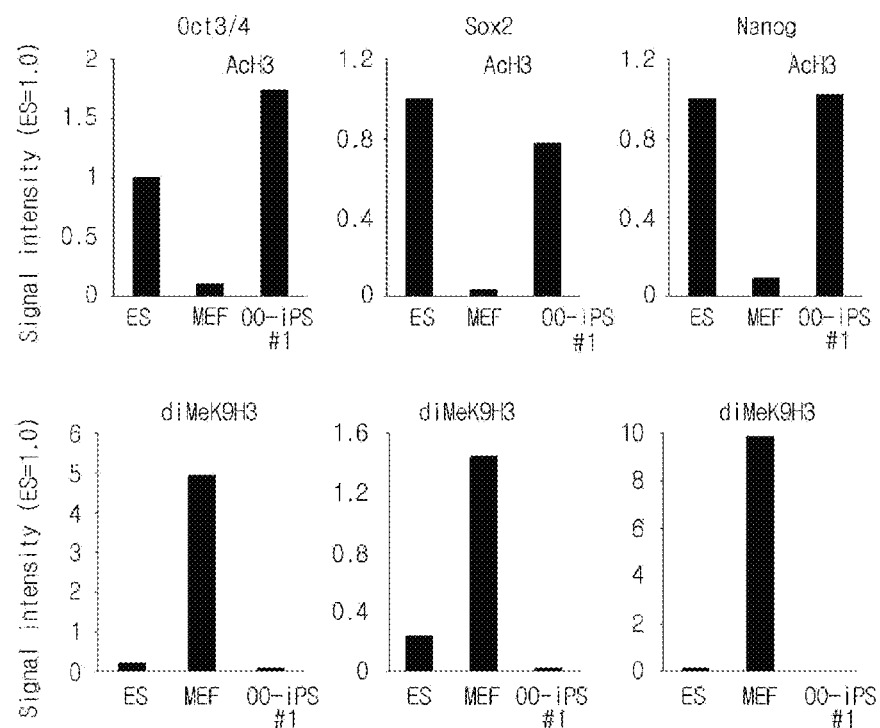
Figure 24A:
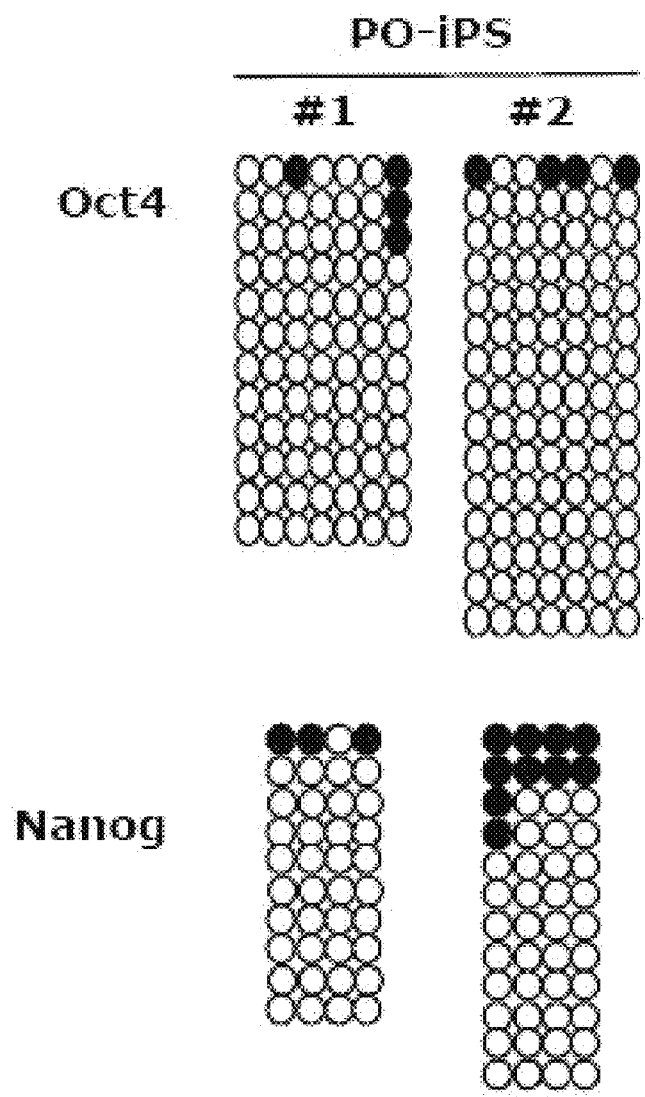
FIGS. 24A and 24B show the epigenetics of the embryonic stem cell-like cells according to the present invention.
Figure 24B:
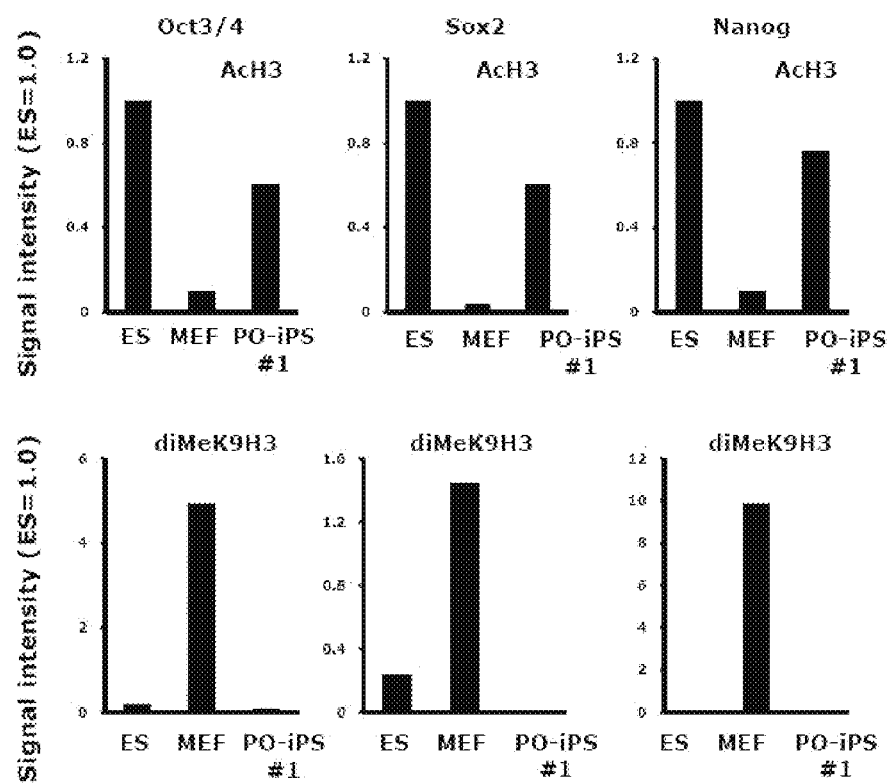

SO-iPS, OO-iPS, and PO-iPS were analyzed for the methylation status of the promoter regions of Oct4 and Nanog, known as being essential for the self-renewal of ES cells, in comparison with ES cells. Bisulfite genomic sequencing analysis showed that the Oct4 and Nanog promoter regions were demethylated in the iPS cells relative to the parental fibroblast lines (FIGS. 11A, 16A and 24A). Chromatin immunoprecipitation analysis revealed that the Oct4, Sox2, and Nanog promoters had increased acetylation of histone H3, indicating the activation of gene expression (FIGS. 11B, 16B and 24B). In contrast, demethylation was detected at lysine 9 of histone H3 of mouse embryonic fibroblasts (FIGS. 11B, 16B and 24B). Data was quantified by real-time PCR with corresponding primers for the Oct4, Sox2 and Nanog promoters following a ChIP assay.

Example 12

Global Gene Expression in Comparison with ES Cells

Figure 17:
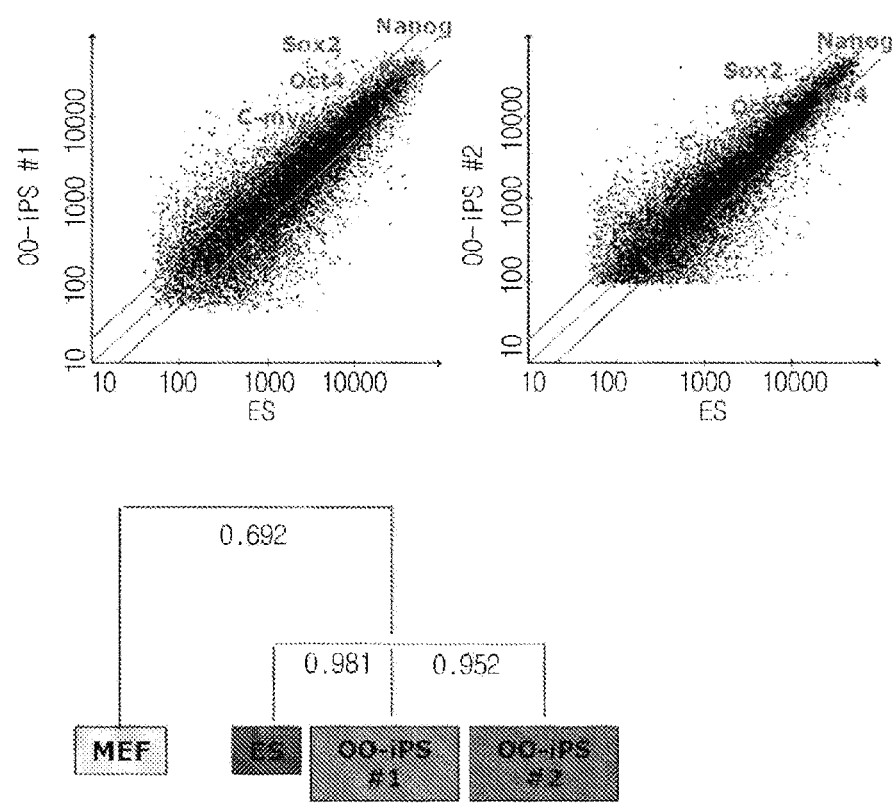
FIG. 17 shows the global gene expression profiles of ES and OO-iPS cells, obtained by DNA microarray analysis. OO-iPS cells are found to be similar in gene expression pattern to mES cells (upper panel), as analyzed by scatter plots of the global gene expression profiles. A Pearson correlation analysis shows a high correlation between ES cells and SO-iPS cells, with a correlation coefficient of 0.98. The clones of the induced stem cells have a Pearson correlation coefficient of 0.95 with respect to ES cells.
Figure 25:
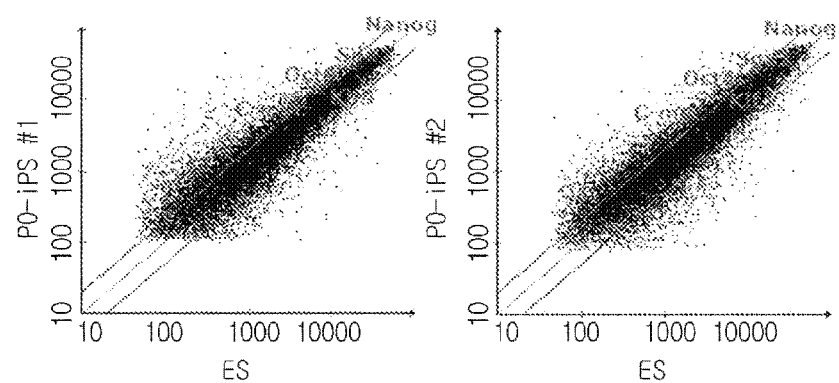
FIG. 25 shows the global gene expression profiles of ES and PO-iPS cells, obtained by DNA microarray analysis. PO-iPS cells are found to be similar in gene expression pattern to mES cells, as analyzed by scatter plots of the global gene expression profiles. A Pearson correlation analysis shows a high correlation between ES cells and PO-iPS cells, with a correlation coefficient of 0.97 and 0.95.
Figure 25:
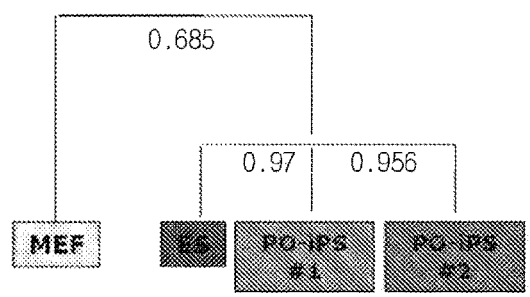

The global gene expressions of SO-iPS, OO-iPS and PO-iPS cells were analyzed and compared to those of ES cells using DNA microarray assays. Scatter plots of the global gene expression showed that the expression of the most genes was within the range of 2-fold changes and that Oct4, Sox2, Nanog, c-myc, Klf4, known as being essential for ES cells, were expressed in similar patterns between the induced stem cells and ES cells (FIGS. 12, 17 and 25).

Figure 12:
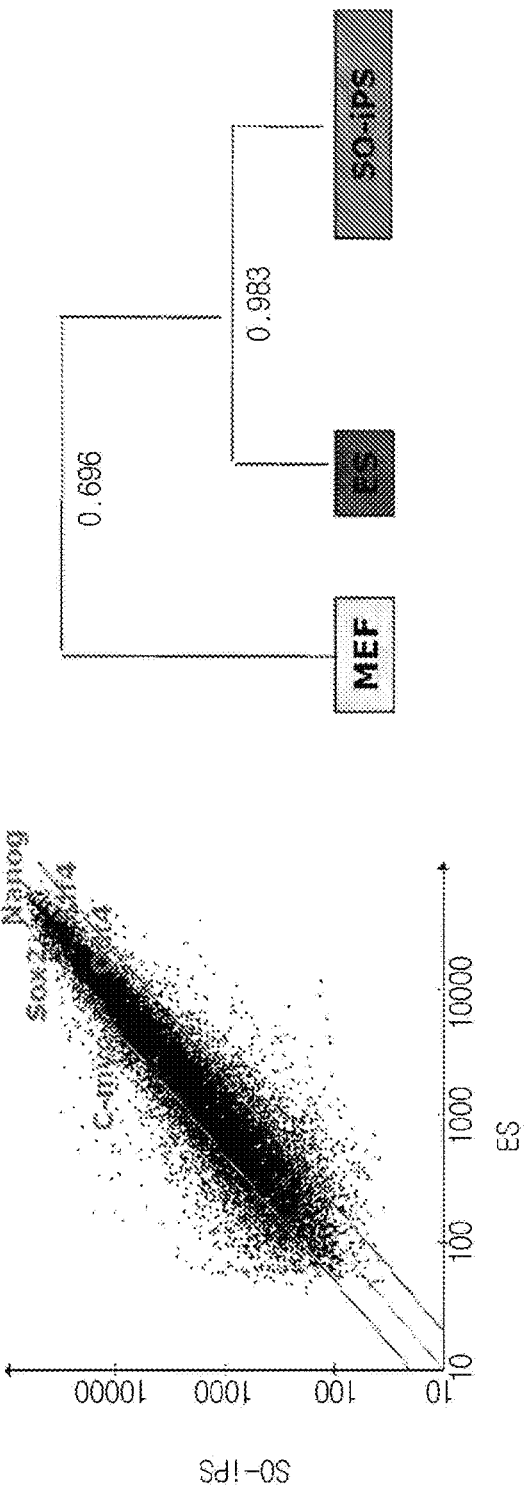
FIG. 12 shows the global gene expression profiles obtained by DNA microarray analysis. BO-iPS cells are found to be similar in gene expression pattern to mES cells, as analyzed by scatter plots of the global gene expression profiles. A Pearson correlation analysis shows a high correlation between ES cells and SO-iPS cells, with a correlation coefficient of 0.98.

High correlation between SO-iPS cells and ES cells was confirmed by a Pearson correlation coefficient of 0.98 (FIG. 12).

The same results as the above were observed for the clones of OO-iPS cells. A Pearson correlation coefficient of 0.98 indicated a high correlation between OO-iPS cells and ES cells. One of the clones was also highly correlated with ES cells as demonstrated by a coefficient of 0.95 (FIG. 17).

The same results as the above were observed in OO-iPS cells treated with different concentrations of purmorphamine. Pearson correlations coefficients between the different OO-iPS cells and ES cells were calculated to be 0.97 and 0.95, indicating a high correlation therebetween (FIG. 25).

Example 13

Assay for In-Vitro and In-Vivo Differentiation into Three Germline Layers

Figure 13A:
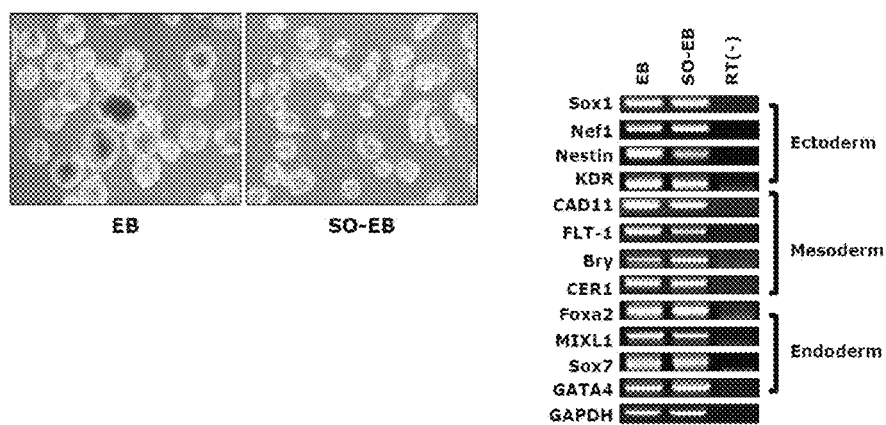
FIGS. 13A to 13C show in-vitro and in-vivo differentiation into all three germ layers.
Figure 13B:
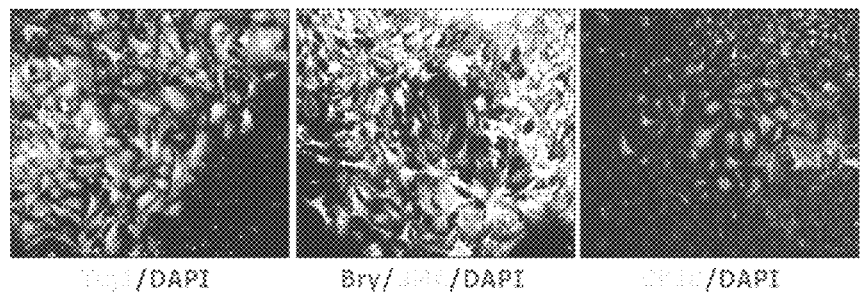
Figure 18A:
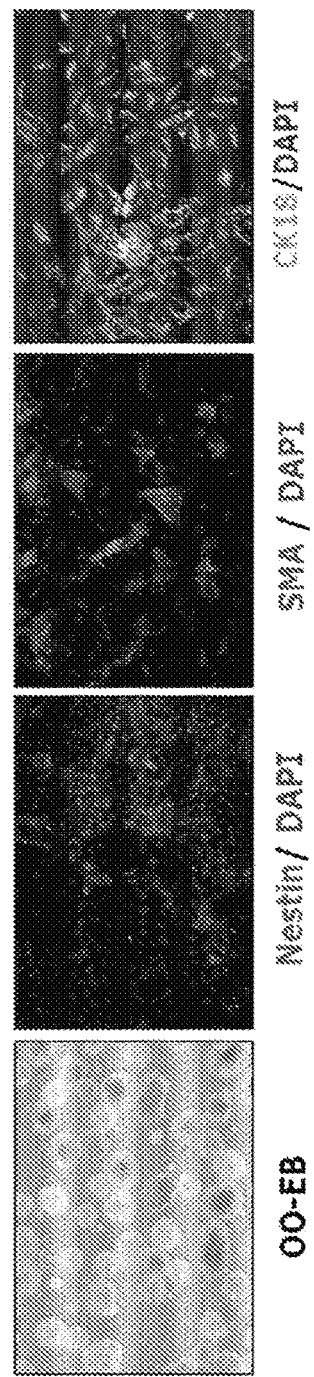
FIGS. 18A and 18B show the in-vitro and in-vivo differentiation of the embryonic stem cell-like cells of the present invention into all three germ layers.
Figure 26A:
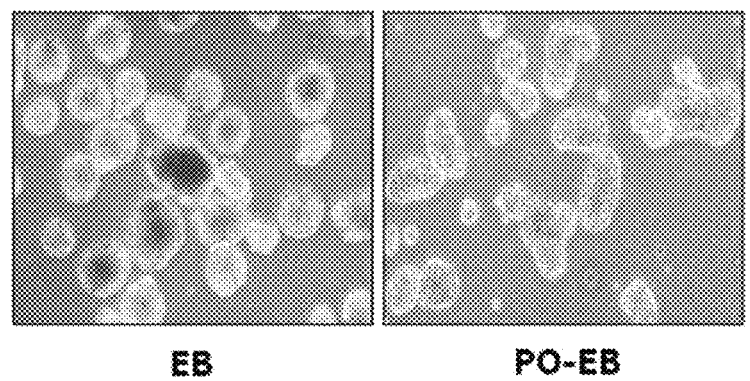
FIGS. 26A to 26D show the in-vitro and in-vivo differentiation potential of the induced embryonic stem cell-like cells according to the present invention into all three germ layers.
Figure 26A:
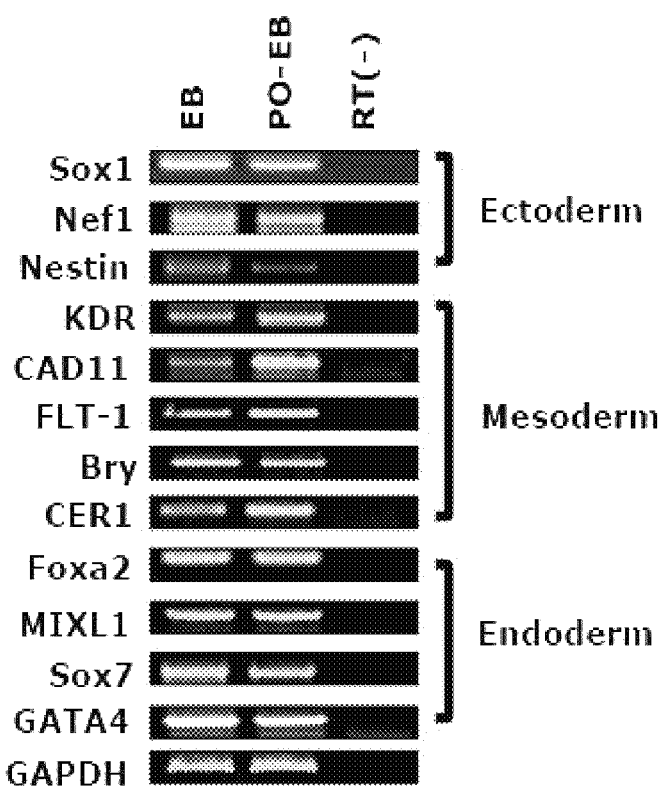
Figure 26B:
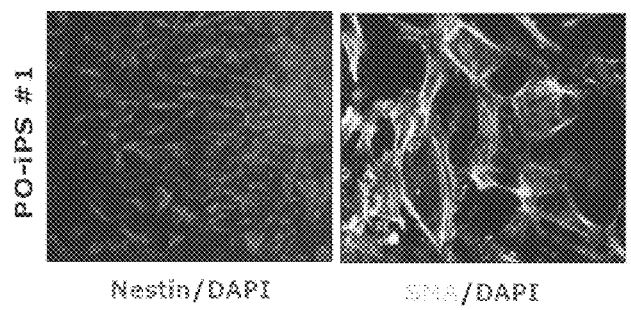

To investigate the differentiation potential of SO-iPS cells in vitro, first, they were examined for embryonic body (EB) formation (FIGS. 13A, 18A and 26A). On day 7 after EB formation, the embryonic bodies were found to express the genes characteristic of the three germ layers in the same patterns as ES cells, as measured by RT-PCR (FIGS. 13A and 26A, right panel). Embryonic bodies were replated onto 0.1% gelatin-coated plates. Spontaneous differentiation was examined by immunostaining for representative lineage specific markers with the indicated antibodies. An immunochemical staining assay detected the expression of Tuj1, bry, SMA, and CK18 in SO-iPS cells, the expression of Nestin, SMA and CK18 in OO-iPS cells, and the expression of Tuj1 and SMA in PO-iPS, indicating in-vitro differentiation into the three germ cells (FIGS. 13B, 18A and 26A).

Figure 13C:
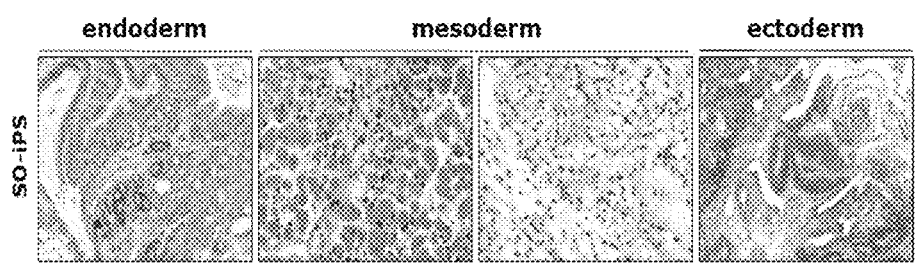
Figure 18B:
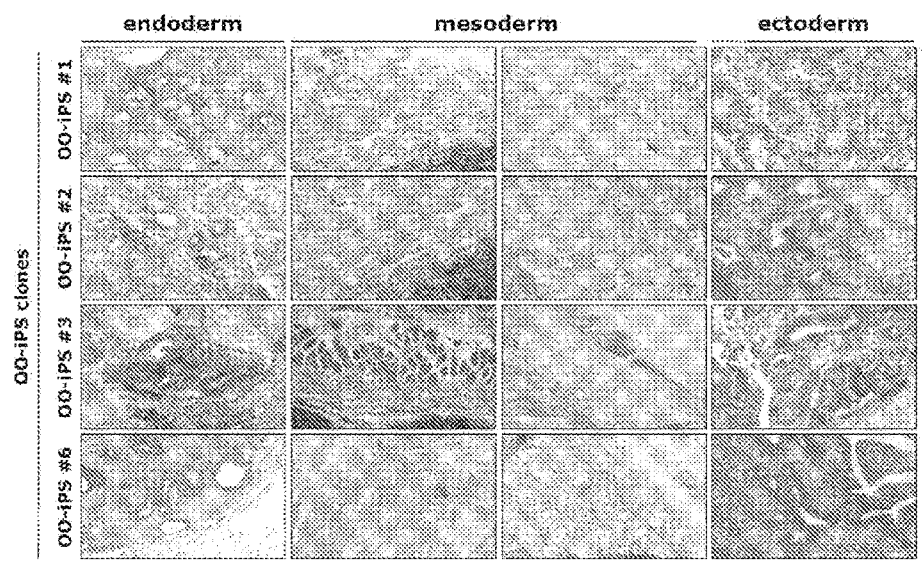
Figure 26C:
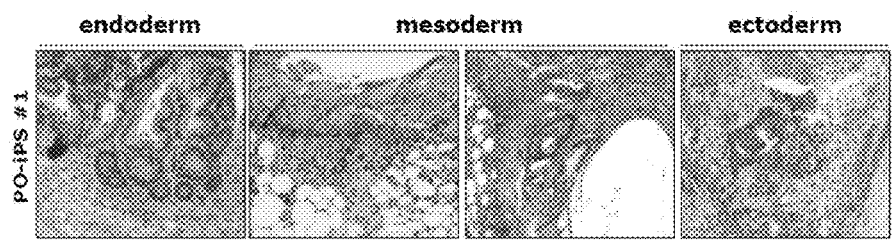
Figure 26D:
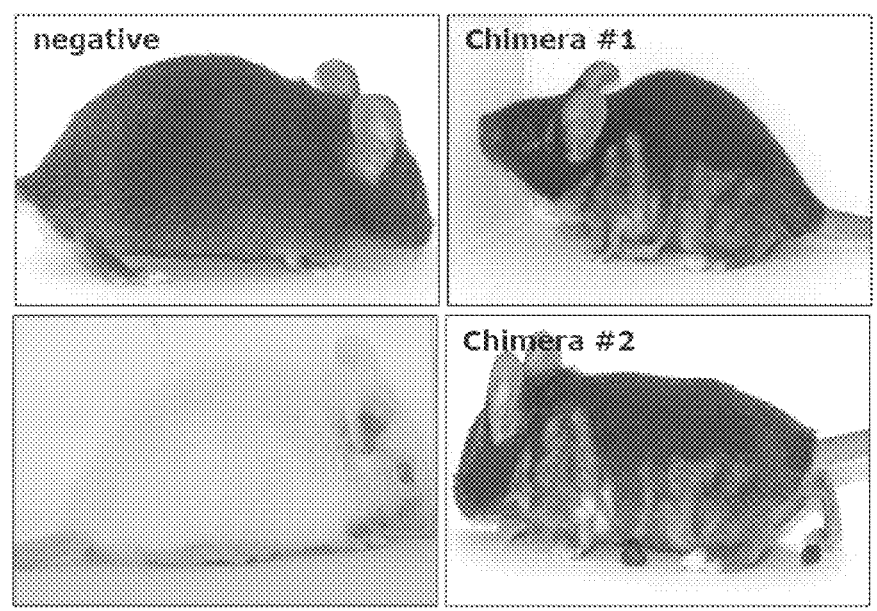

To investigate the differentiation potential of iPS cells in vivo, they were assayed for teratoma formation. $1 \times 10^6$ cells were centrifuged at 8000 rpm for 5 min and the pellet thus obtained was cultured at 37° C. for 24 hrs in a proliferation medium for embryonic stem cells, followed by injecting the cells under the kidney capsule into the dorsal flank of 6-week-old Balb/c nude mice. Eight to ten weeks later, the kidney was excised, embedded in paraffin, and processed for H&E staining. The results showed differentiation of the iPS cells into cells corresponding to the three germ lines, confirming the teratoma formation thereof (FIGS. 13C, 18B and 26C). As for PO-iPS cells, they were injected into the blastocysts of C57/BL6. The injected blastocysts were transferred into a surrogate female. Chimeric mice were born at F1. Chimera formation was evident by comparing the surrogate mice with C57/BL6 mice (FIG. 26D). These results demonstrated that BO-iPS cells have properties similar to those of ES cells.

Example 14

Figure 19A:
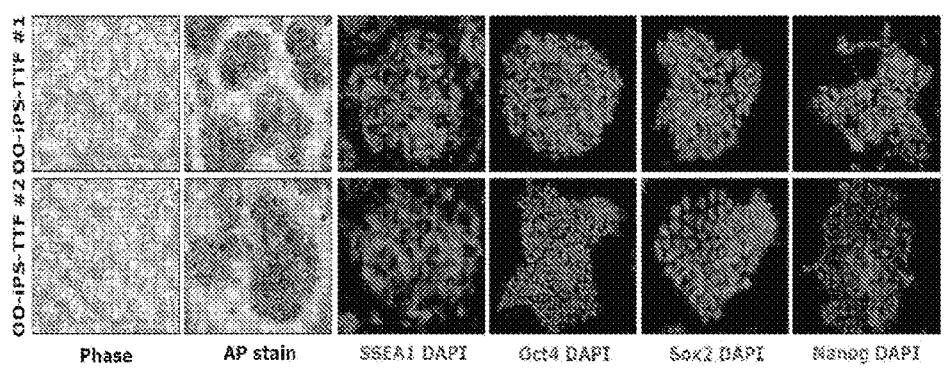
FIGS. 19A and 19B shows the establishment of induced stem cell lines (OO-iPS-TTF #1 and 2) from adult mouse embryonic fibroblasts under the conditions applied to mouse embryonic fibroblasts, and their properties.
Figure 19B:
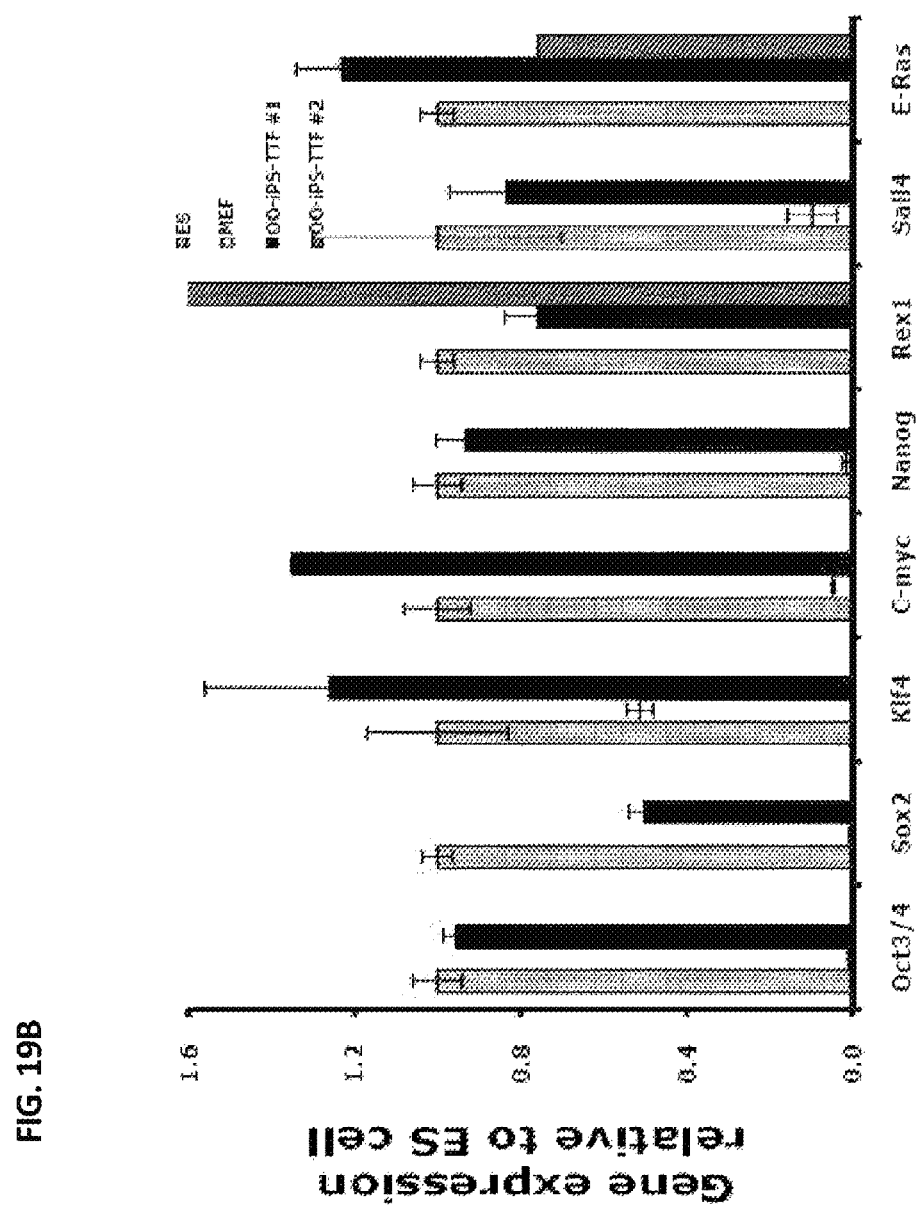

Establishment of iPS Cells (OO-iPS-TTF #1,2) from Adult Mouse Embryonic Fibroblasts by Oct4 Introduction while Treatment with Oxysterol The reprogramming method established with mouse embryonic fibroblasts was applied to adult mouse embryonic fibroblasts. The reprogramming method also allowed the derivation of embryonic stem cell-like cells (FIG. 19A), named OO-iPS-TTF #1 and 2, which were obtained upon treatment with different oxysterol concentrations 0.1 µM and 0.5 µM, respectively. 00-iPS-TTF #1 and 2 were positively stained with AP and found to express SSEA1, Oct4, Sox2, and Nanog as measured by immunochemical staining assays (FIG. 19A). Also, quantitative real-time PCR showed that these cells had the same expression patterns of genes essential for self-renewal as do ES cells (FIG. 19B).

Example 15

Epigenic Study of OO-iPS-TTF #1 and 2

Figure 20A:
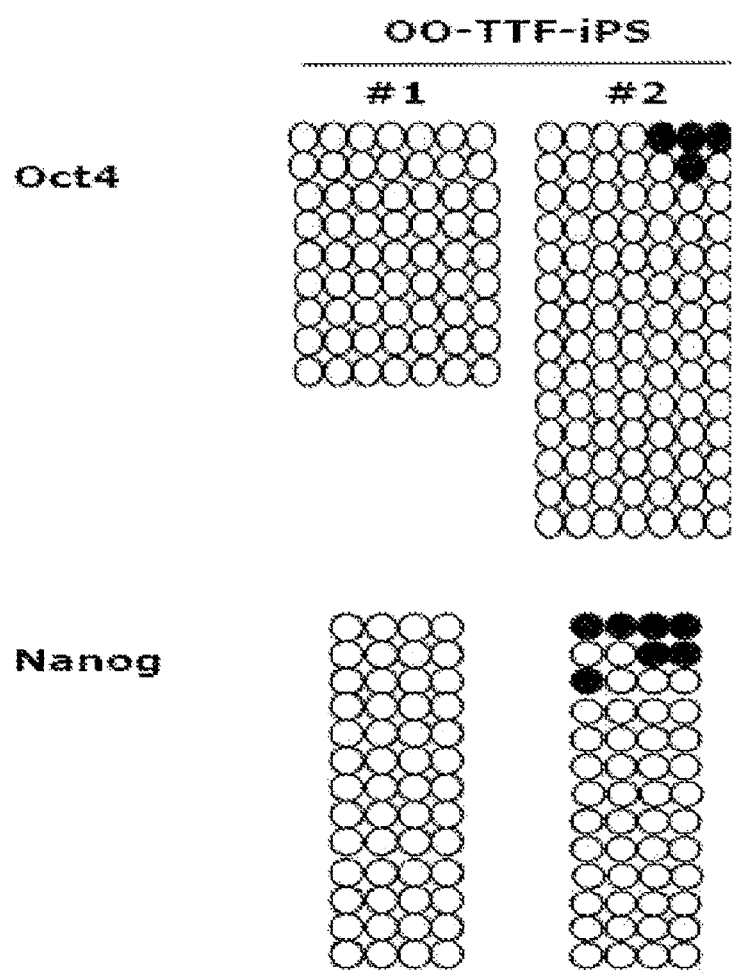
FIGS. 20A and 20B show the epigenetics of the embryonic stem cell-like cells (OO-iPS-TTF #1 and 2) derived from adult mouse fibroblast.
Figure 20B:
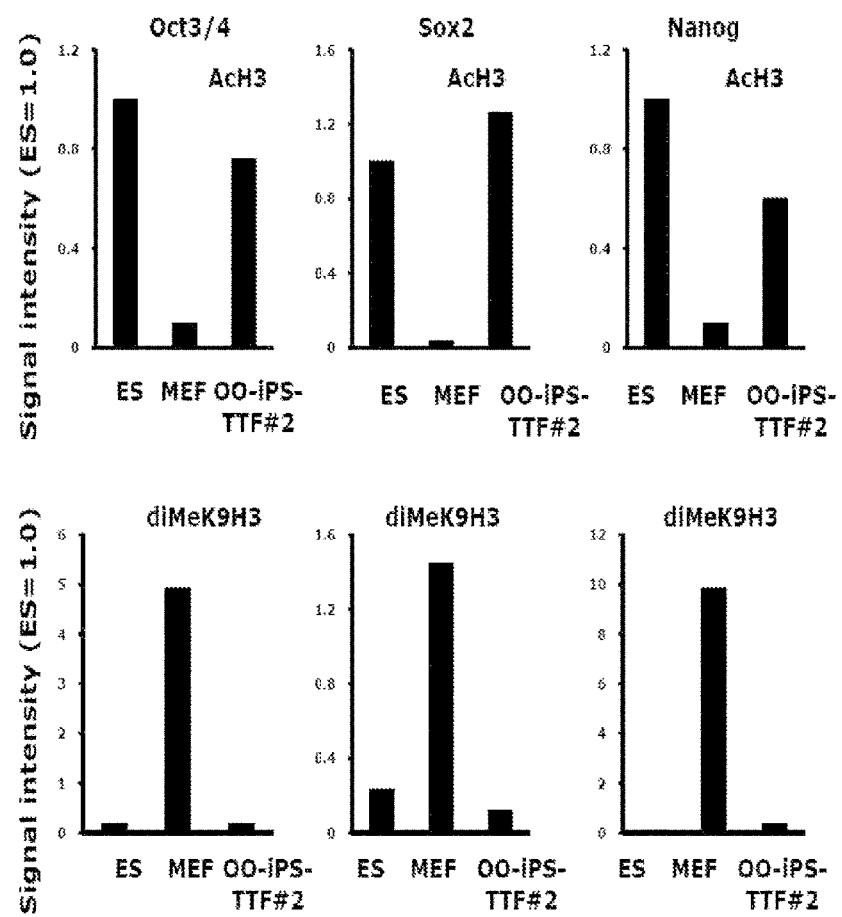

OO-iPS-TTF #1 and 2 were analyzed for the methylation status of the promoter regions of Oct4 and Nanog, known as being essential for the self-renewal of ES cells, for purposes of comparison with ES cells. Bisulfite genomic sequencing analysis showed that the Oct4 and Nanog promoter regions were demethylated in the iPS cells relative to the parental fibroblast lines (FIG. 20A). Chromatin immunoprecipitation analysis revealed that the Oct4, Sox2, and Nanog promoters had increased the acetylation of histone H3, indicating the activation of gene expression (FIG. 20B).

Example 16

Figure 21A:
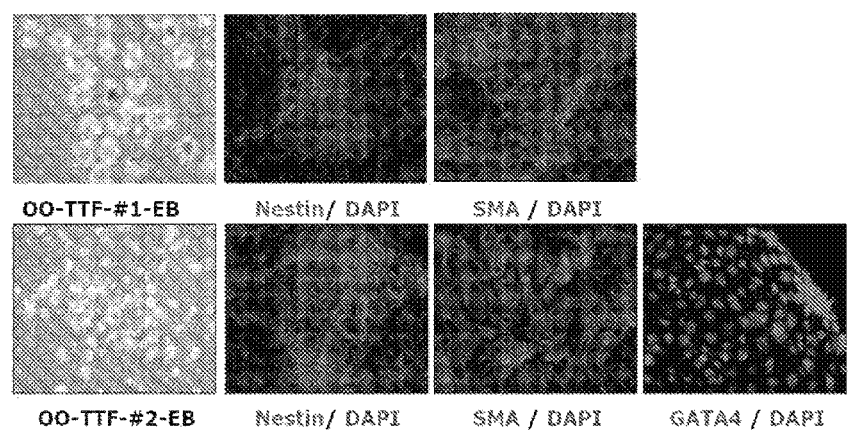
FIGS. 21A and 21B show the in-vitro and in-vivo differentiation potential of the induced embryonic stem cell-like cells (OO-iPS-TTF #1 and 2) derived from adult mouse fibroblasts according to the present invention into all three germ layers.
Figure 21B:
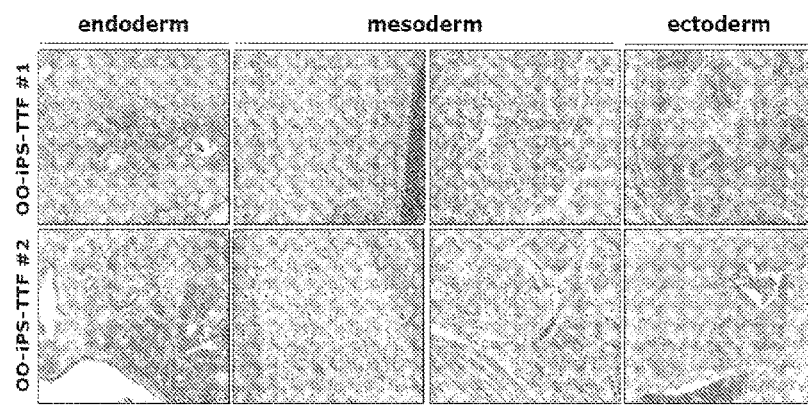

Assay of OO-iPS-TTF #1 and 2 for In-Vitro and In-Vivo Differentiation into Three Germline Layers To investigate the differentiation potential of OO-iPS-TTF #1 and 2 in vitro, first, they were examined for embryonic body (EB) formation. Embryonic bodies were replated onto 0.1% gelatin-coated plates. Spontaneous differentiation was examined by immunostaining for representative lineage specific markers with the indicated antibodies. An immunochemical staining assay detected the expression of Nestin, SMA and GATA4, indicating that OO-iPS-TTF #1 and 2 can form embryonic bodies in vitro and differentiate into the three germ cells in vitro (FIG. 21A). In order to investigate the differentiation potential of OO-iPS-TTF #1 and 2 cells in vivo, the same procedure as was used in experiments with OO-iPS cells was repeated. Eight to ten weeks later, the kidney was excised, embedded in paraffin, and processed for H&E staining. The results showed the differentiation of the OO-iPS-TTF #1 and 2 cells into cells corresponding to the three germ layers, confirming the teratoma formation thereof (FIG. 21B).

As described hitherto, the introduction of an Oct4 gene in combination with a Bmi1 gene or in combination with treating with Shh or a Shh analog such as oxysterol or purmorphamine, followed by culturing under the conditions used for embryonic stem cells induce somatic cells to undergo dedifferentiation into pluripotent stem cells.

In suitable conditions, the induced embryonic stem cell-like cells prepared according to the present invention can differentiate into, for example, cardiomyocytes, insulin-producing cells, or neurons which are thus useful in cell therapy for various diseases including cardiac dysfunction, insulin-dependent diabetes, Parkinson's diseases, spinal cord injury, etc. Thus, the induced embryonic stem cell-like cells are promising solutions to the problems occurring with human embryos, that is, the death of a human embryo and immunological rejection. In addition, various cells (e.g., cardiomyocytes, hepatocytes, etc.) differentiated from the iPS cells are used as systems for evaluating chemicals, drugs, poisons, etc. for medicinal efficacy or toxicity.

Further, a Shh protein, which is an upstream regulator of Bmi1, or a Shh analog, such as oxysterol or purmorphamine, can used, instead of Bmi1 gene, to reprogram somatic cells to generate iPS cells, such that an Oct4 gene alone is utilized for transfection, which results in reducing the number of the genetic factors conventionally needed. Furthermore, the present invention provides a technique on the basis of which a method can be provided for generating iPS cells without introducing genes.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for reprogramming somatic cells to generate induced mouse pluripotent stem cells, comprising steps of:
  (i) simultaneously treating mouse fibroblasts with a Shh (Sonic hedgehog signaling) protein, oxysterol, purmorphamine, and a packaging cell expressing a vector encoding Oct4, wherein the treated fibroblasts are cultured in a neural stem cell media containing DMEM/F12, B27, N2, bFGF, and EGF
  (ii) culturing the cells produced from step (i) in an embryonic stem cell culture conditions including DMEM, LIF, and a feeder layer;

thereby producing induced mouse pluripotent stem cells.

* * * * *